United States Patent
Dull et al.

(10) Patent No.: US 6,627,648 B1
(45) Date of Patent: Sep. 30, 2003

(54) PHARMACEUTICAL COMPOSITIONS AND METHODS FOR USE

(75) Inventors: Gary Maurice Dull, Lewisville, NC (US); Erin E. Reich, Nashville, TN (US); Jared Miller Wagner, Stillwater, OK (US); Balwinder Singh Bhatti, Winston-Salem, NC (US); Michael B. Consilvio, Potomac, MD (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/928,984

(22) Filed: Aug. 13, 2001

Related U.S. Application Data

(63) Continuation of application No. 09/317,327, filed on May 24, 1999.

(51) Int. Cl.[7] .................... A61K 31/44; C07D 213/02; C07D 213/65
(52) U.S. Cl. .................. 514/351; 514/351; 514/357; 546/300; 546/315; 546/334
(58) Field of Search .......................... 514/351; 546/300, 546/303

(56) References Cited

U.S. PATENT DOCUMENTS

| | | | |
|---|---|---|---|
| 4,599,336 A | 7/1986 | Carson et al. | 514/259 |
| 4,927,838 A | 5/1990 | Guthrie et al. | 514/337 |
| 5,212,188 A | 5/1993 | Caldwell et al. | 514/343 |
| 5,585,388 A | 12/1996 | Cosford et al. | 514/343 |
| 5,597,919 A | 1/1997 | Dull et al. | 544/242 |
| 5,604,231 A | 2/1997 | Smith et al. | 514/256 |
| 5,616,707 A | 4/1997 | Crooks et al. | 544/242 |
| 5,616,716 A | 4/1997 | Dull et al. | 546/300 |
| 5,629,325 A | 5/1997 | Lin et al. | 514/318 |
| 5,663,194 A | 9/1997 | Mewshaw | 514/456 |
| 5,663,356 A | 9/1997 | Ruecroft et al. | 546/300 |
| 5,686,473 A | 11/1997 | Cosford et al. | 514/357 |
| 5,726,316 A | 3/1998 | Crooks et al. | 546/311 |
| 5,731,314 A | 3/1998 | Bencherif et al. | 514/256 |
| 5,736,560 A | 4/1998 | Cosford et al. | 514/343 |
| 5,811,442 A | 9/1998 | Bencherif et al. | 514/384 |
| 5,824,692 A | 10/1998 | Lippiello et al. | 514/343 |
| 5,852,041 A | * 12/1998 | Cosford et al. | 514/351 |
| 5,861,423 A | 1/1999 | Caldwell et al. | 514/351 |
| 5,885,998 A | 3/1999 | Bencherif et al. | 514/256 |
| 6,218,383 B1 | 4/2001 | Bencherif | 514/214.01 |
| 6,232,316 B1 | 5/2001 | Dull et al. | 514/256 |
| 6,262,124 B1 | 7/2001 | Dull et al. | 514/649 |
| 6,274,606 B1 | 8/2001 | Caldwell et al. | 514/345 |

FOREIGN PATENT DOCUMENTS

| | | | | |
|---|---|---|---|---|
| EP | 0 142 057 A2 | 5/1985 | | C07D/513/04 |
| EP | 0 230 035 A3 | 7/1987 | | C07D/403/12 |
| EP | 0 559 413 A1 | 9/1993 | | A61K/31/465 |
| EP | 0 571 139 A1 | 11/1993 | | A61K/31/44 |
| EP | 0 230 035 B1 | 10/1994 | | C07D/403/12 |
| EP | 0 230 035 A2 | 7/1997 | | C07D/403/12 |
| JP | 63234466 | 11/1988 | | |
| WO | WO94/08992 | 4/1994 | | C07D/401/12 |
| WO | wO95/12612 | 5/1995 | | C07K/5/078 |
| WO | WO96/31475 | 10/1996 | | C07D/213/38 |
| WO | WO96/40682 | 12/1996 | | C07D/401/12 |
| WO | WO 97/19059 A1 | 5/1997 | | C07D/207/08 |
| WO | WO97/40011 | 10/1997 | | C07D/213/38 |
| WO | WO97/42205 | 11/1997 | | C07D/17/08 |
| WO | WO98/25920 | 6/1998 | | C07D/401/12 |
| WO | WO99/51216 | 10/1999 | | A61K/31/00 |
| WO | WO00/62767 | 10/2000 | | A61K/31/00 |
| WO | WO00/75110 A1 | 12/2000 | | C07D/213/74 |

OTHER PUBLICATIONS

Abreo et al., "Novel 3–Pyridyl Ethers with Subnanomolar Affinity for Central Neuronal Nicotonic Acetylcholine Receptors," *J. Med. Chem.*, 39: 817–825 (1996).

Arora et al., "Preparation and Biological Evaluation of a Potential Photoaffinity Label for the Prostaglandin $H_2$/Thromboxane $A_2$ Receptor," *J. Med. Chem.*, 30: 918–924 (1987).

Bannon et al., "Broad–Spectrum, Non–Opiod Analgesic Activity by Selective Modulation of Neuronal Nicotinic Acetylcholine Receptors," *Science*, 279: 77–81 (Jan. 2, 1998).

Bencherif et al., "RJR–2403: A Nicotinic Agonist with CNS Selectivity I. In Vitro Characterization," *J. of Pharmacology and Exper. Therapeutics*, 279(3): 1413–1421 (1996).

B. Bleicher & N. Cosford, "Aryl–and Heteroaryl–Alkyne Coupling Reactions Catalyzed by Palladium on Carbon and CuI in an Aqueous Medium," *Synlett*, 1115–1116 (Nov., 1995).

Bremmer et al., "Synthesis of 5–aryl–1, 4–benzoxazepine and 6–Phenyl–2H–1,5–benzoxazocine Derivatives," *Aust. J. Chem.*, 37: 129–141 (1984).

Armin Buschauer, "Phenoxy–and Phenylthioalkylguanidines: Synthesis and in vitro Pharmacology," *Eur. J. Med. Chem.*, 23: 1–6 (1998).

(List continued on next page.)

*Primary Examiner*—Alan L. Rotman
*Assistant Examiner*—Janet L Coppins
(74) *Attorney, Agent, or Firm*—Womble Carlyle Sandridge & Rice, PLLC

(57) ABSTRACT

Patients susceptible to or suffering from conditions and disorders, such as central nervous system disorders, are treated by administering to a patient in need thereof aryloxyalkylamines and arylthioalkylamines, including pyridyloxyl-alkylamines, phenoxyalkylamines, pyridylthiolalkylamines and phenylthio-alkylamines. Exemplary compounds include (2-(5-bromo(3-pyridylthio))-ethyl)methylamine, (2-(5-bromo(3-pyridylthio))isopropyl)methylamine, (2-(5-bromo(3-pyridylthio))propyl)methylamine, (3-(5-bromo(3-pyridylthio))-propyl)methylamine, 3-((3S)-3-pyrrolidinyloxy)pyridine, 3-(4-piperidinyloxy)pyridine, 3-(1-methyl-4-piperidinyloxy)pyridine, (3-benzo[3,4-d]1,3-dioxolan-5-yloxypropyl)methylamine, and methyl(3-tricyclo[7.3.1.0<5,13>]tridec-2-yloxypropyl)amine.

33 Claims, No Drawings

OTHER PUBLICATIONS

Elliott et al., "2–(Aryloxymrthyl) Azacyclic Analogues as Novel Nicotinic Acetylcholine Receptor (nAChR) Ligands," *Bioorganic & Medicinal Chemistry Letters*, 6(19): 2283–2288 (1996).

Elliott et al., "Novel 2–(2'–Furo[3,2–b]Pyridinyl) Pyrrolidines: Potent Neuronal Nicotinic Acetylcholine Receptor Ligands," *Bioorganic & Medicinal Chemistry Letters*, 7(21): 2703–2708 (1997).

Grail et al., "Derivatives of Dimethylaminoethanol and Dimethylaminoethylamine," *The Journal of American Chemical Society*, LXXIV: 1313–1315 (Jan.–Mar., 1952).

Guthrie et al.; "Pentadienyl Carboxamide Derivatives as Antagonists of Platelet–Activating Factor," *J. Med. Chem.* 32(8) 1820–1835 (1989).

Holladay et al., "Identification and Initial Structure–Activity Relationships of (R)–5–(2–Azetidinylmethoxy)–2–chloropyridine (ABT–594), a Potent, Orally Active, Non–Opiate Analgesic Agent Acting via Neuronal Nicotinic Acetycholine Receptors," *Journal of Medical Chemistry*, 41(4): 407–412 (Feb. 12,1998).

Holladay et al., "Neuronal Nicotinic Acetylcholine Receptors as Targets for Drug Discovery," *Journal of Medicinal Chemistry*, 40(26): 4169–4194 (Dec. 19, 1997).

International Search Report, PCT/US99/04235, Date of Mailing: Sep. 29, 1999.

International Search Report, PCT/US00/11256; Date of Mailing: Mar. 8, 2001.

Ismaiel et al., "2–(1–Naphthyloxy)ethylamines with Enhanced Affinity for Human $5-HT_{1D\beta}$ ($h5-HT_{1B}$) Serotonin Receptors," *J. Med. Chem.*, 40(26): 4415–4419 (1997).

Iwakura et al., "Cyclizations of Thioureas with a Hydroxy Group at the β–Position of the N–Substituent. I. Reaction with Cupric Acetate," *Bulletin of the Chemical Society of Japan*, 43(8): 2531–2535 (1970).

Kawase et al., "Mode of Action of 3–Substituted Propylamine Cytotoxicity in Culture Cells," *Biochemical Pharmacology*, 31(18): 2983–2988 (1982).

Lever et al., "Monocyclic Pteridine Analogues. Inhibition of *Escherichia coli* Dihydropteroate Synthase by 6–Amino–5–nitrosoisocytosines," *J. Med. Chem.*, 28: 1870–1874 (1985).

Lin et al., "Structure–Activity Studies on 2–Methyl–3–(2(S)–Pyrrolidinylmethoxy)Pyridine (ABT–089): An Orally Bioavailable 3–Pyridyl Ether Nicotinic Acetylcholine Receptor Ligand with Cognition–Enhancing Properties," *J. Med. Chem.*, 40: 385–390 (1997).

Lin et al., "Synthesis and Structure–Activity Relationships of Pyridine–Modified Analogs of 3–[2((S)–Pyrrolidinyl)–Methoxy]Pyridine, A–84543, A Potent Nicotinic Acetylcholine Receptor Agonist," *Bioorganic & Medicinal Chemistry Letters*, 8: 249–254 (1998).

Lippiello et al., "RJR–2403: A Nicotine Agonist with CNS Selectivity II. In Vivo Characterization," *J. of Pharmacology and Exper. Therapeutics*, 279(3): 1422–1429 (1996).

Mewshaw et al., "New Generation Dopaminergic Agents. 1. Discovery of a Novel Scaffold Which Embraces the $D_2$ Agonist Pharmacophore. Strucutre–Activity Relationships of a Series of 2–(Aminomethyl)chromans," *J. Med. Chem.*, 40(26) 4235–4256 (1997).

Mitani et al., "Novel Phenoxyalkylamine Derivatives. IV. Synthesis, $Ca^{2+}$–Antagonistic Activity and Quantitative Structure–Activity Analysis of α–Isopropyl–α–[3–[3–(3–methoxyphenoxy)propylamino]propyl]–α–phenylacetonitrile Derivatives," *Chem. Pharm. Bull.*, 36(10): 4103–4120 (1988).

Mutai et al., "Photocyclization in 3–[107 –(Anilino)Alkoxy] Nitrobenzenes," *Chemistry Letters*, 931–932 (1978).

Pierson et al., "Design and Synthesis of Propranolol Analogues as Sertotonergic Agents," *J. Med. Chem.*, 32: 859–863 (1989).

Schaeffer et al., "Inhibition of Synaptosomal Accumulation of *l*–Norepinephrine II: N–Aryloxyalkylphentermines, Quaternary *d*–Amphetamines, and 3–Aryloxypropylamines," *J. of Pharm. Sciences*, 65(1): 122–126 (1976).

Tilley et al., "N–(Heterocyclic alkyl)pyrido[2,1–*b*] quinazoline–8–carboxamides as Orally Active Antiallergy Agents," *J. Med. Chem.*, 30: 185–193 (1987).

Unangst et al., "(Aryloxy(alkylamines as Selective Human Dopamine $D_4$ Receptor Antagonists: Potential Antipsychotic Agents," *J. Med. Chem.*, 40: 4026–4029 (1997).

Wubbels et al., "Regioselectivity of Photochemical and Thermal Smiles Rearrangements and Related Reactions of β–(Nitrophenoxy)ethylamines," *J. Org. Chem.*, 50: 4499–4504 (1985).

Wubbles et al., "α–Cyclodextrin Complexation as a Probe of Heterolytic General Base–Catalyzed Photo–Smiles Rearrangements," *Tetrahedron Letters*, 30(47): 6477–6480 (1989).

Wubbles et al., "Brønsted Catalysis Law Plots for Heterolytic, General Base–Catalyzed Smiles Photorearrangement," *J. Org. Chem.*, 60: 2960–2961 (1995).

Mitani et al., "Novel Phenoxyalkylamine Derivatives II. Synthesis and $Ca^{2+}$–Antagonistic Activities of α–Alkyl–α–[(phenoxypropylamino)propyl]–benzeneacetonitrile Derivatives," *Chem. Pharm. Bull.*, 36(1): 373–385 (1988).

* cited by examiner

PHARMACEUTICAL COMPOSITIONS AND METHODS FOR USE

This is a continuation application claiming priority to application Ser. No. 09/317,327 filed May 24, 1999, the disclosure of which is incorporated herein by reference in its entirety.

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem.* & *Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279:77–80 (1998), PCT WO 94/08992, PCT WO 96/31475, PCT WO 96/40682, and U.S. Pat. No. 5,583,140 to Bencherif et al., U.S. Pat. No. 5,597,919 to Dull et al. U.S. Pat. No. 5,604,231 to Smith et al. and U.S. Pat. No. 5,852,041 to Cosford et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but which compound when employed in an amount sufficient to effect the functioning of the CNS, does not significantly effect those receptor subtypes which have the potential to induce undesirable side effects (e.g., appreciable activity at skeletal muscle sites).

SUMMARY OF THE INVENTION

The present invention relates to aryloxyalkylamines, including pyridyloxyalkylamines and phenoxyalkylamines. Exemplary compounds include dimethyl(2-(3-pyridyloxy) ethylamine, dimethyl(4-(3-pyridyloxy)butyl)amine, 2-(3-pyridyloxy)ethylamine, 4-(3-pyridyloxy)butylamine, methyl(3-(5-methoxy-3-pyridyloxy)propyl)amine, ethyl(3-(3-pyridyloxy)propyl)amine, methyl(2-(3-pyridyloxy)ethyl) amine, methyl(3-(6-methyl(3-pyridyloxy))propyl)amine, (3-(3-methoxyphenoxy)propyl)methylamine, (3-(5-chloro(3-pyridyloxy))-1-methylpropyl)methylamine, dimethyl(3-(3-pyridyloxy)propyl)amine, 3-(3-pyridyloxy)propylamine, methyl(4-(3-pyridyloxy)butyl)amine, 3-(5-chloro-3-pyridyloxy)propylamine, methyl(3-(5-isopropoxy-3-pyridyloxy)propyl)amine, (3-(5-chloro(3-pyridyloxy)) propyl)methylamine, methyl(3-(5-(phenylmethoxy)(3-pyridyloxy))propyl)amine, methyl(3-(2-methyl(3-pyridyloxy))propyl)amine, (methylethyl)(3-(3-pyridyloxy) propyl)amine, benzyl(3-(3-pyridyloxy)propyl)amine, cyclopropyl(3-(3-pyridyloxy)propyl)amine, methyl(1-methyl-3-(3-pyridyloxy)propyl)amine, methyl(3-(3-nitrophenoxy)propyl)amine, 1-(3-chloropropoxy)-3-nitrobenzene, (3-(3-aminophenoxy)propyl)methylamine, dimethyl(3-(3-(methylamino)propoxy)phenyl)amine, methyl(3-tricyclo[7.3.1.0<5,13>]tridec-2-yloxypropyl) amine, (3-benzo[3,4-d]1,3-dioxolan-5-yloxypropyl)

methylamine, 3-(4-piperidinyloxy)pyridine, 3-((3S)-3-pyrrolidinyloxy)pyridine, (2-(5-bromo(3-pyridylthio))ethyl)methylamine, (2-(5-bromo(3-pyridylthio))isopropyl)methylamine, (2-(5-bromo(3-pyridylthio))propyl)methylamine and (3-(5-bromo(3-pyridylthio))propyl)methylamine. The present invention also relates to prodrug derivatives of the compounds of the present invention.

The present invention also relates to methods for the prevention or treatment of a wide variety of conditions or disorders, and particularly those disorders characterized by disfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastro-intestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds of the formula I:

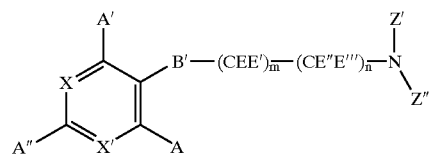

where each of X and X' are individually nitrogen, N—O or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., Chem. Rev. 91:165 (1991); and m is an integer and n is an integer such that the sum of m plus n is 1, 2, 3, 4, 5, 6, 7, or 8, preferably is 1, 2, or 3, and more preferably is 2 or 3, and most preferably 3. B' is oxygen or sulfur, but most preferably is oxygen. Z' and Z" individually represent hydrogen or lower alkyl (e.g., straight chain or branched alkyl including $C_1$–$C_8$, preferably $C_1$–$C_5$, such as methyl, ethyl, or isopropyl), Z' and Z" individually represent hydrogen, alkyl (e.g., straight chain or branched alkyl including $C_1$–$C_8$, preferably $C_1$–$C_5$, such as methyl, ethyl, or isopropyl), substituted alkyl, acyl, alkoxycarbonyl, or aryloxycarbonyl; and preferably at least one of Z' and Z" is hydrogen or both of Z' and Z" are hydrogen, and most preferably Z' is hydrogen and Z" is methyl. Alternatively, Z' is hydrogen and Z" represents a ring structure (cycloalkyl, heterocyclyl or aryl), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl, thiazolyl or oxazolyl (where any of the foregoing can be suitably substituted with at least one substituent group, such as alkyl, alkoxyl, halo, or amino substituents); alternatively Z' is hydrogen and Z" is propargyl; alternatively Z', Z", and the associated nitrogen atom can form a ring structure such as aziridinyl, azetidinyl, pyrrolidinyl, piperidinyl, morpholinyl, 2-imino-2,3-dihydrothiazolyl or 2-imino-2,3-dihydrooxazolyl, and in certain situations, piperazinyl (e.g., piperazine); Z' and E''' (when n is 1) and the associated carbon and nitrogen atoms can combine to form a monocyclic ring structure such as azetidinyl, pyrrolidinyl, piperidinyl, piperazinyl, or a bicyclic ring structure such as 3-(2-azabicyclo[4.2.0]octyl), 3-(2-azabicyclo[2.2.2]octyl), or 3-(2-azabicyclo[2.2.1]heptyl); however it is preferred that when Z' and E''' and the associated carbon and nitrogen atoms combine to form such a ring, neither E" nor E' are substituted or unsubstituted aryl, heteroaryl, benzhydryl or benzyl; Z', Z" and E" (when n is 1) and the associated carbon and nitrogen atoms can combine to form a bicyclic ring structure such as quinuclidinyl, 2-(1-azabicyclo[2.2.1]-heptyl), or 2-(1-azabicyclo[3.3.0]octyl), or a tricyclic ring structure such as azaadamantyl; Z', E" and E''' (when n is 1) and the associated carbon and nitrogen atoms can combine to form a bicyclic ring structure such as 1-(2-azabicyclo [2.2.1]heptyl); and Z', Z", E" and E''' (when n is 1) and the associated carbon and nitrogen atoms can combine to form a tricyclic ring structure. E, E', E" and E''' individually represent hydrogen or a suitable non-hydrogen substituent (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl), preferably lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl). Generally all of E, E', E" and E''' are hydrogen, or at least one of E, E', E" and E''' is non-hydrogen and the remaining E, E', E" and E''' are hydrogen. In addition, E and E' or E" and E''' and their associated carbon atom can combine to form a ring structure such as cyclopentyl, cyclohexyl or cycloheptyl; or E''' and E' (when located on immediately adjacent carbon atoms) and their associated carbon atoms can combine to form a ring structure such as cyclopentyl, cyclohexyl or cycloheptyl. Depending upon the selection of E, E', E" and E''', compounds of the present invention have chiral centers, and the present invention relates to racemic mixtures of such compounds as well as enamiomeric compounds. For certain compounds, X is nitrogen; for other compounds X' is nitrogen or N—O; and for other compounds X and X' both are nitrogen. Most preferably, X' is nitrogen. Adjacent substituents of A, A' or A" (when X or X' are carbon bonded to a substituent component) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities. For certain preferred compounds X' is C—NR'R", C—OR' or C—NO$_2$, more preferably C—NH$_2$, C—NHCH$_2$ or C—N(CH$_3$)$_2$, with C—NH$_2$ being most preferred. In addition, when X is carbon bonded to a substituent species, it is preferred that the substituent species is H, Br or OR', where R' preferably is benzyl, methyl, ethyl, isopropyl, isobutyl or tertiary butyl. A, A', A" and the substituents of either X or X' (when each respective X and X' is carbon) can include H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl and substituted arylalkyl functionalities. More specifically, X and X' include N, N—O, C—H, C—F, C—Cl, C—Br, C—1, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen or lower alkyl (e.g., C$_1$–C$_{10}$ alkyl, preferably C$_1$–C$_5$ alkyl, and more preferably methyl, ethyl, isopropyl or isobutyl), an aromatic group-containing species or a substituted aromatic group-containing species, and q is an integer from 1 to 6. R' and R" can be straight chain or branched alkyl, or R' and R" can form a cycloalkyl funtionality (e.g., cyclopropyl cyclobutyl, cyclopentyl, cyclohexyl, cycloheptyl, adamantyl, and quinuclidinyl). Representative aromatic group-containing species include pyridinyl, quinolinyl, pyrimidinyl, phenyl, and benzyl (where any of the foregoing can be suitably substituted with at least one substituent group, such as alkyl, halo, or amino substituents). Other representative aromatic ring systems are set forth in Gibson et al., *J. Med. Chem.* 39:4065 (1996). When X and X' represent a carbon atom bonded to a substituent species, that substituent species often has a sigma m value which is between about −0.3 and about 0.75, and frequently between about −0.25 and about 0.6. In certain circumstances the substituent species is characterized as having a sigma m value not equal to 0. A, A' and A" individually represent those species described as substituent species to the aromatic carbon atom previously described for X and X'; and usually include hydrogen, halo (e.g., F, Cl, Br, or I), alkyl (e.g., lower straight chain or branched C$_{1-8}$ alkyl, but preferably methyl or ethyl), or NX"X''' where X" and X''' are individually hydrogen or lower alkyl, including C$_1$–C$_8$, preferably C$_1$–C$_5$ alkyl. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. Depending upon the identity and positioning of each individual E, E, E" and E''', certain compounds can be optically active. Typically, the selection of E, E', E" and E''' is such that up to about 4, and frequently up to 3, and usually 0, 1 or 2, of the substituents designated as E, E', E" and E''' are non-hydrogen substituents (i.e., substituents such as lower alkyl or halo-substituted lower alkyl). Typically, X is CH, CBr or COR. Most preferably, X' is nitrogen.

As employed herein, "alkyl" refers to straight chain or branched alkyl radicals including C$_1$–C$_8$, preferably C$_1$–C$_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including C$_1$–C$_8$, preferably C$_1$–C$_5$ and having at least one carbon-carbon double bond; "substituted alkenyl" refers to alkenyl radicals further bearing one or more substituent groups as defined above; "cycloalkyl" refers to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above; "acyl" refers to straight chain or branched alkyl- or substituted alkyl-carbonyl radicals including C$_1$–C$_8$, preferably C$_1$–C$_5$, such as formyl, acetyl, or propanoyl; "alkoxycarbonyl" refers to an alkyl or substituted alkyl radical attached to an O-carbonyl moiety; and "aryloxycarbonyl" refers to an aryl or substituted aryl radical attached to an O-carbonyl moiety.

One representative compound is (3-(3-pyridyloxy)propyl)amine, for which X is CH, X' is N, B' is O, n is 0, m is 3, and A, A', A", E, E', Z' and Z" are weach H. One representative compound is (3-(5-bromo-(3-pyridyloxy)propyl)methylamine, for which X is C—Br, X' is N, B' is O, n is 0, m is 3, A, A', A", E, E" and Z' are each H, and Z" is methyl. One representative compound is (1-methyl-3-(3-pyridyloxy)propyl)methylamine, for which X is CH, X' is N, B' is O, n is 1, m is 2, A, A', A", E, E', E" and Z' are each H, and E''' and Z" are methyl. One representative compound is (3-(5-ethoxy-(3-pyridyloxy)propyl)methylamine, for which X is C—OCH$_2$CH$_3$, X' is N, B' is O, n is 0, m is 3, A, A', A", E, E' and Z' are each H, and Z" is methyl. One representative compound is (3-(6-methyl-(3-pyridyloxy)propyl)methylamine, for which X is CH, X' is N, B' is O, n is 0, m is 3, A, A', E, E' and Z' are each H, and A" and Z" each are methyl. One representative compound is (3-(5-chloro-(3-pyridyloxy)propyl)methylamine, for which X is C—Cl, X' is N, B' is O, n is 0, m is 3, A, A', A", E, E' and Z' are each H, and Z" is methyl. One representative compound is (3-(2-bromo(3-pyridyloxy)propyl)methylamine, for which X is CH, X' is N, B' is O, n is 0, m is 3, A is Br, A', A", E, E' and Z' are each H, and Z" is methyl. One representative compound is (1-methyl-3-(5-methoxy-(3-pyridyloxy)propyl))methylamine, for which X is C—OCH$_3$, X' is N, B' is O, n is 1, m is 2, A, A', A", E, E', E" and Z' are each H, and E'" and Z" are each methyl. One representative compound is (4-(3-pyridyloxy)butyl))methylamine, for which X is CH, X' is N, B' is O, n is 0, m is 4, A, A', A", E, E', and Z' are each H, and Z" is methyl. One representative example is (3-phenoxypropyl)methylamine, for which X and X' are each CH, B' is O, n is 0, m is 3, A, A', A", E, E' and Z' are each H, and Z" is methyl. One representative example is (3-(3-aminophenoxy)propyl)methylamine, for which X is CH, X' is C—NH$_2$, B' is O, n is 0, m is 3, A, A', A", E, E' and Z' are each H, and Z" is methyl. One representative example is (3-(4-methoxyphenoxy)propyl)methylamine, for which X and X' are each CH, B' is O, n is 0, m is 3, A, A', E, E' and Z' are each H, A" is OCH$_3$, and Z" is methyl.

Exemplary other compounds that can be made in accordance with the present invention include (2-(5-bromo(3-pyridylthio))ethyl)methylamine, (2-(5-bromo(3-pyridylthio))isopropyl)methylamine, (2-(5-bromo(3-pyridylthio))propyl)methylamine and (3-(5-bromo(3-pyridylthio))propyl)methylamine, dimethyl(2-(3-pyridyloxy)ethylamine, dimethyl(4-(3-pyridyloxy)butyl)amine, 2-(3-pyridyloxy)ethylamine, 4-(3-pyridyloxy)butylamine, methyl(3-(5-methoxy-3-pyridyloxy)propyl)amine, ethyl(3-(3-pyridyloxy)propyl)amine, methyl(2-(3-pyridyloxy)ethyl)amine, methyl(3-(6-methyl(3-pyridyloxy))propyl)amine, (3-(3-methoxyphenoxy)propyl)methylamine, (3-(5-chloro(3-pyridyloxy))-1-methylpropyl)methylamine, dimethyl(3-(3-pyridyloxy)propyl)amine, 3-(3-pyridyloxy)propylamine, methyl(4-(3-pyridyloxy)butyl)amine, 3-(5-chloro-3-pyridyloxy)propylamine, methyl(3-(5-isopropoxy-3-pyridyloxy)propyl)amine, (3-(5-chloro(3-pyridyloxy))propyl)methylamine, methyl(3-(5-(phenylmethoxy)(3-pyridyloxy))propyl)amine, methyl(3-(2-methyl(3-pyridyloxy))propyl)amine, (methylethyl)(3-(3-pyridyloxy)propyl)amine, benzyl(3-(3-pyridyloxy)propyl)amine, cyclopropyl(3-(3-pyridyloxy)propyl)amine, methyl(1-methyl-3-(3-pyridyloxy)propyl)amine, methyl(3-(3-nitrophenoxy)propyl)amine, 1-(3-chloropropoxy)-3-nitrobenzene, (3-(3-aminophenoxy)propyl)methylamine, dimethyl(3-(3-(methylamino)propoxy)phenyl)amine, methyl(3-tricyclo[7.3.1.0<5,13>]tridec-2-yloxypropyl)amine, (3-benzo[3,4-d]1,3-dioxolan-5-yloxypropyl)methylamine, 3-(4-piperidinyloxy)pyridine, 3-((3S)-3-pyrrolidinyloxy)pyridine, methyl(3-(5-(3,4-dimethoxybenzyloxy)(3-pridyloxy))methylamine, methyl(3-(3-quinolyloxy)propyl)amine, 3-(5-bromo-3-pyridylthio))propyl)methylamine and 3-((3S)-(1-methyl-3-pyrrolidinyloxy)pyridine.

The manner in which certain phenoxyalkylamine compounds of the present invention are provided can vary. Certain phenoxyalkylamine compounds can be prepared by the alkylation of phenol with a 1,3-dihalopropane, such as 1,3-dichloropropane, 1,3-dibromopropane, 1,3-diiodopropane, or 1-chloro-3-iodopropane, which are commercially available from Aldrich Chemical Company, in the presence of a base (e.g., sodium hydride) in dry N,N-dimethylformamide. The resulting 3-halo-1-phenoxypropane can be converted to a phenoxyalkylamine, such as methyl(3-phenoxypropyl)amine, by treatment with methylamine in a solvent, such as tetrahydrofuran or aqueous methanol. The manner in which certain 3-substituted-phenyl analogs of (3-phenoxypropyl)methylamine of the present invention can be synthetically prepared is analogous to that described for the preparation of methyl(3-phenoxypropyl)amine with the exception that 3-substituted-phenols are employed rather than phenol. In some instances, protecting groups may be employed when necessary. For example, one representative compound, (3-(3-aminophenoxy)propyl)methylamine can be prepared by the alkylation of an N-phthalamido-protected phenol, 2-(3-hydroxyphenyl)isoindoline-1,3-dione (prepared by treatment of 3-aminophenol with phthalic anhydride) with 1-chloro-3-iodopropane. The resulting intermediate, 2-(3-(3-chloropropoxy)-phenyl)isoindoline-1,3-dione can be converted to (3-(3-aminophenoxy)-propyl)methylamine by treatment with methanolic methylamine. The manner in certain 4-substituted-phenyl analogs of methyl(3-phenoxypropyl)amine of the present invention can be synthetically prepared is analogous to that described for the preparation of methyl(3-phenoxypropyl)amine with the exception that 4-substituted-phenols are employed rather than phenol. For example, 4-methoxyphenol can be converted to (3-(4-methoxyphenoxy)propyl)methylamine.

The manner by which pyridyloxyalkylamine compounds of the present invention are provided can vary. Certain pyridyloxyalkylamine compounds can be prepared by the alkylation of 3-hydroxypyridine with a 1,3-dihalopropane, such as 1,3-dichloropropane, 1,3-dibromopropane, 1,3-diodopropane or 1-chloro-3-iodopropane, which are commercially available from Aldrich Chemical Company, in the presence of a base (e.g., sodium hydride) in dry N,N-dimethylformamide. The resulting 3-halo-1-(3-pyridyloxy)propane can be converted to a pyridyloxyalkylamine, such as (3-(3-pyridyloxy)propyl)methylamine, by treatment with methylamine in a solvent, such as tetrahydrofuran or aqueous methanol. One representative compound, (3-(3-pyridyloxy)propyl)methylamine is prepared by the reaction of 3-hydroxypyridine with 1.2 molar equivalents of 1-chloro-3-iodopropane and 1.6 molar equivalents of sodium hydride in dry N,N-dimethylformamide at ambient temperature. The resulting intermediate, 3-chloro-1-(3-pyridyloxy)propane, obtained in about 54% yield, is converted to (3-(3-pyridyloxy)propyl)methylamine in about 40% yield, by treatment with an excess (25 molar equivalents) of aqueous methylamine in methanol, assisted by heating. Certain pyridyloxyalkylamine compounds, such as (4-(3-pyridyloxy)-butyl)methylamine, can be prepared by alkylating 3-hydoxypyridine with a 1,4-dihalobutane, such as 1,4-diiodobutane, 1,4-dibromobutane, 1,4-dichlorobutane or 1-chloro-4-iodobutane, which are commercially available from Aldrich Chemical Company, in the presence of a base (e.g., sodium hydride) in N,N-dimethylformamide. The resulting 4-halo-1-(3-pyridyloxy)butane can be converted to a pyridyloxyalkylamine, such as (4-(3-pyridyloxy)butyl) methylamine, by treatment with methylamine in a solvent, such as tetrahydrofuran or aqueous methanol.

The manner by which certain 2-substituted-3-pyridyl analogs of (3-(3-pyridyloxy)propyl)methylamine and certain 6-substituted-3-pyridyl analogs of (3-(3-pyridyloxy)propyl)methylamine of the present invention can be synthetically prepared is analogous to that described for the preparation of (3-(3-pyridyloxy)propyl)methylamine with the exception that 2-substituted-3-hydroxypyridines and 6-substituted-3-hydroxypyridines are employed rather than 3-hydroxypyridine. For example, using such methodology, commercially available 2-bromo-3-hydroxypyridine and 3-hydroxy-2-nitropyridine can be converted to 3-(2-bromo (3-pyridyloxy))propyl)methylamine and 3-(2-nitro(3-pyridyloxy))propyl)methylamine, respectively. Similarly, commercially available 3-hydroxy-6-methylpyridine can be converted to 3-(6-methyl(3-pyridyloxy))propyl) methylamine.

The manner by which certain 5-substituted-3-pyridyl analogs of (3-(3-pyridyloxy)propyl)methylamine of the present invention can be synthesized is analogous to that described for (3-(3-pyridyloxy)propyl)methylamine, with the exception that 5-substituted-3-hydroxypyridines are employed rather than 3-hydroxypyridine. For example, using such a methodology, 5-bromo-3-hydroxypyridine can be converted to the intermediate, 3-chloro-1-(5-bromo-3-pyridyloxy) propane, which is converted to 3-(5-bromo(3-pyridyloxy)) propyl)methylamine. 5-Bromo-3-hydroxypyridine can be prepared form 2-furfurylamine using the procedure described in U.S. Pat. No. 4,192,946 to Clauson-Kaas et al. the disclosure of which is incorporated herein by reference in its entirety. In a similar manner, 5-chloro-3-hydroxypyridine, which is commercially available from Aldrich Chemical Company, can be converted to 3-(5-chloro (3-pyridyloxy))propyl)methylamine. Similarly, 5-methoxy-3-hydroxypyridine, prepared according to the procedures set forth in Chen et al., *Heterocycles* 24(12): 3411 (1986), can be converted to 3-(5-methoxy(3-pyridyloxy))propyl) methylamine. Similarly, 5-ethoxy-3-hydroxypyridine can be converted to 3-(5-ethoxy(3-pyridyloxy))propyl) methylamine. Similarly, 5-amino-3-hydroxypyridine, prepared according to the procedures set forth in Tamura et al., *Heterocycles* 15(2): 871 (1981), can be converted to 3-(5-amino(3-pyridyloxy))propyl)methylamine. In a similar manner, 3-hydroxy-5-trifluoromethylpyridine and 2-fluoro-5-hydroxy-3-methylpyridine, each prepared using methods set forth in PCT WO 96/40682, can be converted to 3-(5-trifluoromethyl(3-pyridyloxy))propyl)methylamine and 3-(6-fluoro-5-methyl(3-pyridyloxy))propyl)methylamine, respectively.

A number of 5-substituted analogs, such as (3-(5-substituted(3-pyridyloxy))propyl)methylamine, can be synthesized from 5-substituted 3-hydroxypyridines, which can be prepared from 5-amino-3-hydroxypyridine via a diazonium salt intermediate. For example, 5-amino-3-hydroxypyridine can be converted to 5-fluoro-3-hydroxypyridine, 5-chloro-3-hydroxypyridine, 5-bromo-3-hydroxypyridine, 5-iodo-3-hydroxypyridine or 5-cyano3-hydroxypyridine, using the general techniques set forth in Zwart et al., *Recueil Trav. Chim. Pays-Bas* 74: 1062 (1955). Futhermore, 5-hydroxy-substituted analogs can be prepared from the reaction of the corresponding 5-diazonium salt intermediate with water. The 5-fluoro-substituted analogs can be prepared from the reaction of the 5-diazonium salt intermediate with fluoroboric acid. The 5-chloro-substituted analogs can be prepared from the reaction of 5-amino-3-hydroxypyridine with sodium nitrite and hydrochloric acid in the presence of copper chloride. The 5-cyano-substituted analogs can be prepared from the reaction of the corresponding diazonium salt intermediate with potassium copper cyanide. The 5-amino-substituted analogs can be converted to the corresponding 5-nitro analogs by reaction with fuming sulfuric acid and peroxide according to the general techniques described in Morisawa, *J. Med. Chem.* 20: 129 (1977), for converting an amino pyridine to a nitropyridine.

Certain pyridyloxyalklylamines that possess a branched side chain, such as (1-methyl-3-(3-pyridyloxy)propyl) methylamine, can be prepared by alkylating 3-hydroxypyridine with a protected 3-hydroxy-1-halobutane, such as 3-[(tert-butyl)dimethylsilyloxy]-1-bromobutane (prepared according to the procedures set forth in Gerlach et al., *Helv. Chim. Acta.* 60(8): 2860 (1977)), thereby producing a (tert-butyl)dimethylsilyl protected 4-(3-pyridyloxy)butan-2-ol. The (tert-butyl)dimethylsilyl group can be removed by treatment with ammonium fluoride or aqueous acetic acid to give 4-(3-pyridyloxy)butan-2-ol. Mesylation or tosylation of that compound with methanesulfonyl chloride in triethylamine or p-toluenesulfonyl chloride in pyridine, followed by treatment with methylamine in tetrahydrofuran or aqueous methanol, provides a compound having a methyl branched side chain (e.g., (1-methyl-3-(3-pyridyloxy)propyl)methylamine).

Alternatively, pyridyloxyalkylamines possessing a branched side chain, such as (1-methyl-3-(3-pyridyloxy) propyl)methylamine, can be synthesized by alkylating 3-hydroxypyridine with a protected 1-iodo-3-butanone, namely 2-methyl-2-(2-iodoethyl)-1,3-dioxolane, with is prepared according to the procedures set forth in Stowell et al., *J. Org. Chem.* 48: 5381 (1983). The resulting ketal, 3-(2-(1-methyl-2,5-dioxolanyl)ethoxy)pyridine, can be protected by treatment with aqueous acetic acid or p-toluenesulfonic acid in methanol to yield 4-(3-pyridyloxy)butan-2-one. Reductive amination of the resulting ketone using methylamine and sodium cyanoborohydride according to the methodology set forth in Borch, *Org. Syn.* 52: 124 (1972) provides (1-methyl-3-(3-pyridyloxy)propyl)methylamine. Alternatively, the intermediate, 4-(3-pyridyloxy)butan-2-one, can be reduced with sodium borohydride to yield an alcohol, 4-(3-pyridyloxy)butan-2-ol. Mesylation or tosylation of that alcohol, followed by mesylation or tosylation displacement using methylamine, provides the branched chain pyridyloxyalkylamine, (1-methyl-3-(3-pyridyloxy) propyl)methylamine.

Chiral starting materials are available for the synthesis of the pure enantiomers of the branched chain pyridyloxyalkylamines, such a (1-methyl-3-(3-pyridyloxy) proyl)methylamine. One approach can be carried out using either methyl (R)-(−)-3-hydroxybutyrate or the (+)-enantiomer, (S)-(+)-3-hydroxybutyrate, both of which are available from Aldrich Chemical Company. For example, (R)-(−)-3-hydroxybutyrate can be converted to (R)-(−)-3-tetrahydropyranyloxybutyl bromide, using the procedures set forth in Yuasa et al., *J. Chem. Soc., Perk. Trans.* 1(5): 465 (1996). Alkylation of 3-hyroxypyridine with (R)-(−)-3-tetrahydropyranyloxybutyl bromide using sodium hydride in N,N-dimethylformamide produces the tetrahydropyranyl ether of 4-(3-pyridyloxy)butan-2R-ol. Removal of the tetrahydropyranyl protecting group of that compound using p-toluenesulfonic acid monohydrate in methanol affords 4-(3-pyridyloxy)butan-2R-ol. The resulting chiral alcohol can be elaborated to the chiral pyridyloxyalkylamine, (1S-3-(3-pyridyloxy)propyl)methylamine using a two-step sequence involving tosylation and methylamine displacement of the intermediate tosylate. In a similar process, (S)-(+)-3-hydroxybutyrate can be converted to (S)-(+)-3-tetrahydropyranyloxybutyl bromide using the procedures set forth in Sakai et al., *Agric. Biol. Chem.* 50(6): 1621 (1986). This protected bromo alcohol can be converted to the corresponding chiral pyridyloxyalkylamine, methyl(1R-3-(3-pyridyloxy)propyl)amine, using a sequence involving alkylation of 3-hydroxypyridine, removal of the tetrahydropyranyl group, tosylation, and methylamine displacement of the intermediate tosylate.

The manner by which certain 5-alkoxy-3-pyridyl analogs of methyl(3-(3-pyridyloxy)propyl)amine of the present invention can be synthesized is analogous to that described for the synthesis of methyl(3-(3-pyridyloxy)propyl)amine with the exception that 5-alkoxy-3-hydroxypyridines are employed rather than 3-hydroxypyridine. For example, 3,5-dibromopyridine (commercially available from Aldrich Chemical Company and Lancaster Synthesis Inc.) can be converted to the synthetic intermediate, 5-(3,4-dimethoxybenzyloxy)-3-bromopyridine by heating at 100° C. with veratryl alcohol (3,4-dimethoxybenzyl alcohol) in the presence of sodium and copper powder. The resulting 5-(3,4-dimethoxybenzyloxy)-3-bromopyridine can be heated at 180° C. with concentrated aqueous ammonia in the presence of copper(II) sulfate or copper (I) bromide to produce the aminopyridine compound, 5-(3,4-dimethoxybenzyloxy)-3-aminopyridine. The latter compound can be diazotized and the diazonium salt hydrolyzed by treatment with sodium nitrite and aqueous sulfuric acid to give the hydroxypyridine, 5-(3,4-dimethoxybenzyloxy)-3-hydroxypyridine. This 5-substituted-3-hydroxypyridine can be alkylated with 1-chloro-3-iodopyridine in the presence of sodium hydride in N,N-dimethylformamide to yield 3-chloro-1-(5-(3,4-dimethoxybenzyloxy)-3-pyridyloxy) propane. Treatment of the latter compound with an excess of methylamine in methanol will afford methyl(3-(5-(3,4-dimethoxybenzyloxy)(3-pyridyloxy))propyl)methylamine.

Certain commercially available fused polycyclic haloaromatics can be used as starting materials to prepare compounds of the present invention which possess fused rings. For example, 3-bromoquinoline (commercially available from Aldrich Chemical Company) can be converted to 3-aminoquinoline by heating at about 180° C. with aqueous ammonia in the presence of copper(II) sulfate or copper(I) bromide. The resulting 3-aminoquinoline (commercially available from Aldrich Chemical Company) can be diazotized and subsequently hydrolyzed by treatment with sodium nitrite and aqueous sulfuric acid to produce 3-hydroxyquinoline according to the methodology of C. Naumann and H. Langhals, *Synthesis* (4): 279–281 (1990). 3-Hydroxyquinoline can be alkylated with 1-chloro-3-iodopyridine in the presence of sodium hydride and N,N-dimethylformamide to give 3-chloro-1-(3-quinolyloxy) propane. Treatment of the latter compound with aqueous methylamine will give methyl(3-(3-quinolyloxy)propyl) amine.

Compounds of the present invention possessing a thioether moiety can be prepared from an appropriately substituted pyridine such as 3,5-dibromopyridine (commercially available from Aldrich Chemical Company and Lancaster Synthesis Inc.). As an example, 3,5-dibromopyridine can be treated with 3-mercapto-1-propanol in the presence of sodium hydroxide and N,N-dimethylformamide to give 3-(5-bromo-3-pyridylthio)propan-1-ol. Treatment of the latter compound with p-toluenesulfonyl chloride, followed by treatment of the intermediate tosylate with aqueous methylamine will afford 3-(5-bromo-3-pyridylthio))propyl) methylamine.

Compounds of the present invention that are ethers and possess a cyclic amine functionality can be prepared from hydroxypyridines and hydroxylated cyclic amines using the general coupling method of O. Mitsunobu, *Synthesis:* 1 (1981). For example, 3-((3S)-(1-methyl-3-pyrrolidinyloxy) pyridine can be synthesized by the coupling of 3-hydroxypyridine and (3R)-N-(tert-butoxycarbonyl)-3-hydroxypyrrolidine in the presence of triphenylphosphine and diethyl azodicarboxylate in tetrahydrofuran. The resulting intermediate, 3-((3S)-N-(tert-butoxycarbonyl)-3-pyrrolidinyloxy)pyridine can then be treated with a strong acid such as trifluoroacetic acid to remove the tert-butoxycarbonyl protecting group to produce 3-((3S)-3-pyrrolidinyloxy)pyridine. The latter compound can be N-methylated to afford 3-((3S)-(1-methyl-3-pyrrolidinyloxy)pyridine. Methylation methods employing aqueous formaldehyde and sodium cyanoborohydride as described by M. A. Abreo et al., *J. Med. Chem.* 39: 817–825 (1996) can be used. The N-protected starting material, (3R)-N-(tert-butoxycarbonyl)-3-hydroxypyrrolidine can be prepared from (R)-(+)-3-pyrrolidinol (commercially available from Aldrich Chemical Company) according to the general techniques described by P. C. Houghton et al., *J. Chem. Soc. Perkin Trans* 1 (Issue 13): 1421–1424 (1993). Such a compound is exemplary of a compound whereby E and Z' and their associated carbon atoms, combine to form a ring; and in a similar manner, if m=0, Z' and E''' can combine to form a ring.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the reoccurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. The present invention also relates to prodrug derivatives of the compounds of the present invention. The compounds normally are not optically active. However, certain compounds can possess substituent groups of a character so that those compounds possess optical activity. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Compounds of the present invention are useful for treating those types of conditions and disorders for which other types of nicotinic compounds have been proposed as therapeutics. See, for example, Williams et al. *DN&P* 7(4): 205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al the disclosures of which are incorporated herein by reference in their entirety. Compounds of the present invention can be used as analgesics, to treat ulcerative colitis, to treat a variety of neurodegenerative diseases, and to treat convulsions such as those that are symtematic of epilepsy. CNS disorders which can be treated in accordance with the present invention include presenile dementia (early onset Alzheimer's disease), senile dementia (dementia of the Alzheimer's type), HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome. Compounds of the present invention also can be used to treat conditions such as syphillis and Creutzfeld-Jakob disease.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available, for example, from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activatie relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 1 ug/kg of patient weight. Often, the compounds of the present invention are administered in an amount from 10 ng to less than 1 ug/kg of patient weight, frequently between about 0.1 ug to less than 1 ug/kg of patient weight, and preferably between about 0.1 ug to about 0.5 ug/kg of patient weight. Compounds of the present invention can be administered in an amount of 0.3 to 0.5 ug/kg of patient weight. For compounds of the present invention that do not induce effects on muscle type nicotinic receptors at low concentrations, the effective dose is less than 50 ug/kg of patient weight; and often such compounds are administered in an amount from 0.5 ug to less than 50 ug/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic dopaminergic receptors of the brain of the patient. As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of certain compounds are less than about 100 uM, often are less than about 10 uM and frequently are less than about 5 uM; and of preferred compounds generally are less than about 1 uM, often are less than about 100 nM, and frequently are less than about 50 nM. Though not preferred, certain compounds possess receptor binding constants of less than 10 uM, and even less than 100 uM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively activating neurotransmitter secretion from nerve ending preparations (i.e., synaptosomes). As such, such compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less, than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder, is essentially ineffective in eliciting activation of certain muscle-type nicotinic receptors at concentration higher than 5 times, preferably higher than 100 times, and more preferably higher than 1,000 times, than those required for activation of dopamine release. This selectivity of certain compounds of the present invention against those ganglia-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, an amelioration to some degree of the reoccurrence of CNS disorders. However, such effective amounts of those compounds are not sufficient to elicit any appreciable side effects, as demonstrated by increased effects relating to skeletal muscle. As such, administration of certain compounds of the present invention provides a car therapeutic window in which treatment of certain CNS disorders is provided, and certain side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than $\frac{1}{5}$, and often less than $\frac{1}{10}$ that amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, acute cholangitis, aphteous stomatitis, arthritis (e.g., rheumatoid arthritis and ostearthritis), neurodegenerative diseases, cachexia secondary to infection (e.g., as occurs in AIDS, AIDS related complex and neoplasia), as well as those indications set forth in PCT WO 98/25619. The pharmaceutical compositions of the present invention can be employed in order to ameliorate may of the symptoms associated with those conditions, diseases and disorders. Thus, pharmaceutical compositions of the present invention can be used in treating genetic diseases and disorders, in treating autoimmune disorders such as lupus, as anti-infectious agents (e.g, for treating bacterial, fungal and viral infections, as well as the effects of other types of toxins such as sepsis), as anti-inflammatory agents (e.g., for treating acute cholangitis, aphteous stomatitis, asthma, and ulcerative colitis), and as inhibitors of cytokines release (e.g., as is desirable in the treatment of cachexia, inflammation, neurodegenerative diseases, viral infection, and neoplasia), The compounds of the present invention can also be used as adjunct therapy in combination with existing therapies in the management of the aforementioned types of diseases and disorders. In such situations, administration preferably is such that the active ingredients of the pharmaceutical formulation act to optimize effects upon abnormal cytokine production, while minimizing effects upon receptor subtypes such as those that are associated with muscle and ganglia. Administration preferably is such that active ingredients interact with regions where cytokine production is affected or occurs. For the treatment of such conditions or disorders, compounds of the present invention are very potent (i.e., affect cytokine production and/or secretion at very low concentrations), and are very efficacious (i.e., significantly inhibit cytokine production and/or secretion to a relatively high degree). Effective doses are most preferably at very low concentrations, where maximal effects are observed to occur. Concentrations, determined as the amount of compound per volume of relevant tissue, typically provide a measure of the degree to which that compound affects cytokine production. For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 1, often does not exceed about 0.75, often does not exceed about 0.5, frequently does not exceed about 0.25 mg/24 hr./patient. In addition, administration of the effective dose is such that the concentration of the compound within the plasma of the patient normally does not exceed 500 pg/ml, often does not exceed 300 pg/ml, and frequently does not exceed 100 pg/ml. When employed in such a manner, compounds of the present invention are dose dependent, and as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention, and should not be construed as limiting thereof. In these examples, all parts and percentages are by weight, unless otherwise noted.

EXAMPLES

Example 1
Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., Biochem, Pharmacol. 22:3099 (1973). Low binding constants indicate that the compounds of the present invention exhibit good high affinity binding to certain CNS nicotinic receptors.

Example 2
Neurotransmitter Release From Brain Synaptosomes

Neurotransmitter release was measured using techniques similar to those previously published (Bencherif M, et al.:. JPET 279:1413–1421, 1996).

Rat brain synaptosomes were prepared as follows: Female Sprague Dawley rats (100–200 g) were killed by decapitation after anesthesia with 70% $CO_2$. Brains are dissected, and hippocampus, striatum, and thalamus isolated, and homogenized in 0.32 M sucrose containing 5 mM HEPES pH 7.4 using a glass/glass homogenizer. The tissue was then centrifuged for 1000×g for 10 minutes and the pellet discarded. The supernatant was centrifuged at 12000×g for 20 minutes. The resultant pellet was re-suspended in perfusion buffer (128 mM NaCl, 1.2 mM $KH_2PO_4$, 2.4 mM KCl, 3.2 mM $CaCl_2$, 1.2 mM $MgSO_4$, 25 mM HEPES, 1 mM Ascorbic acid, 0.01 mM pargyline HCl and 10 mM glucose pH 7.4) and centrifuged for 15 minutes at 25000×g. The final pellet was resuspended in perfusion buffer and placed in a water bath (37° C.) for 10 minutes. Radiolabeled neurotransmitter is added (30 $L^3H$ DA, 20 $L^3H$ NE, 10 $L^3H$ glutamate) to achieve a final concentration of 100 nM, vortexed and placed in a water bath for additional 10 minutes. Tissue-loaded filters is placed onto 11-mm diameter Gelman A/E filters on an open-air support. After a 10-minute wash period, fractions are collected to establish the basal release and agonist applied in the perfusion stream. Further fractions were collected after agonist application to re-establish the baseline. The perfusate was collected directly into scintillation vials and released radioactivity was quantified using conventional liquid scintillation techniques. Release of neurotransmitter was determined in the presence of 10 M of various ligands and was expressed as a percentage of release obtained with a concentration of 10 M (S)-(−)-nicotine or 300 MTMA resulting in maximal effects.

Example 3
Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis. Low $E_{max}$ values at muscle-type receptors indicate that the compounds of the present invention do not induce activation of muscle-type receptors. Such preferable compounds have the capability to activate human CNS receptors without activating muscle-type nicotinic acetylcholine receptors. Thus, there is provided a therapeutic window for utilization in the treatment of CNS disorders. That is, at certain levels the compounds show CNS effects to a significant degree but do not show undesirable muscle effects to any significant degree. The compounds begin to cause muscle effects only when employed in amounts of many times those required to activate dopamine release.

Example 4
Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis. Low $E_{max}$ values at ganglia-type receptors indicate that the compounds of the present invention do not induce activation of ganglia-type receptors. Such preferable compounds have the capability to activate human CNS receptors without activating ganglia-type nicotinic acetylcholine receptors. Thus, there is provided a therapeutic window for utilization in the treatment of CNS disorders. That is, at certain levels the compounds show CNS effects to a significant degree but do not show certain undesirable side effects to any significant degree. The compounds begin to cause effects at ganglia only when employed in amounts of many times those required to activate dopamine release.

Example 5
Synthesis of (2-(5-Bromo(3-pyridylthio))-isopropyl) methylamine Hemigalactarate and (2-(5-Bromo(3-pyridylthio))propyl)methylamine Hemigalactarate
1-(5-Bromo-3-pyridylthio)propan-2-ol Under a nitrogen atmosphere, a mixture of 1-mercapto-2-propanol (3.89 g, 42.21 mmol), sodium hydroxide (1.69 g, 42.21 mmol) and N,N-dimethylformamide (DMF) (40 mL) was heated at 105° C. (oil bath temperature) for 2 h. The resulting solution was cooled to ambient temperature and 3,5-dibromopyridine (8.00 g, 33.77 mmol) was added in one portion using additional DMF (10 mL). The mixture was stirred at ambient temperature for 48 h. The turbid mixture was then heated under nitrogen at 85° C. (oil bath temperature) for 18 h. The mixture was cooled to ambient temperature, diluted with water (250 mL) and extracted with ether (3×75 mL). The combined ether extracts were washed with saturated NaCl solution (100 mL), dried ($Na_2SO_4$), filtered and concentrated to a light-yellow foam (9.19 g). The crude product was purified by column chromatography on silica gel (225 g), eluting with EtOAc-hexane (3:1, v/v). Fractions containing the product ($R_f$ 0.38) were combined and concentrated to give 3.78 g (45.1%) of a light-yellow oil.

(2-(5-Bromo(3-pyridylthio))-isopropyl)methylamine and (2-(5-Bromo(3-pyridylthio))propyl)methylamine Under a nitrogen atmosphere, a cold (0–5° C.), stirring solution of 1-(5-bromo-3-pyridylthio)propan-2-ol (1.80 g, 7.25 mmol) in dichloromethane (8 mL) containing pyridine (3 drops) was treated in one portion with p-toluenesulfonyl chloride (1.452 g, 7.07 mmol). The resulting solution was allowed to warm to ambient temperature over 16 h. TLC analysis on silica gel eluting with EtOAc-hexane (3:1, v/v) indicated an incomplete reaction. Therefore, additional p-toluenesulfonyl chloride (0.28 g, 1.45 mmol), triethylamine (1 mL) and pyridine (1 mL) were added. The mixture was allowed to stir under nitrogen for 48 h. The solution was concentrated on a rotary evaporator to a red oil. The oil was cooled to 0–5° C., basified with saturated $K_2CO_3$ solution (40 mL) and extracted with $CH_2Cl_2$ (3×25 mL). The combined $CH_2Cl_2$ extracts were washed with saturated NaCl solution (50 mL), dried ($Na_2SO_4$), filtered, concentrated (rotary evaporator, using toluene (3×20 mL) to azeotropically remove pyridine) and further dried under high vacuum to afford a dark-red oil (2.65 g). The oil was dissolved in methanol (20 mL) and transferred to a heavy-walled glass pressure-tube apparatus. A 40 wt % aqueous solution of methylamine (80 mL) was added. The tube was sealed and the mixture was stirred and heated at 120° C. for 2.5 h. The resulting brown solution was allowed to cool to ambient temperature and was further stirred for 16 h. The solution was concentrated to a dark-brown oil. At 0–5° C., the oil was basified with 1 M NaOH solution (20 mL) and extracted with $CHCl_3$ (6×20 mL). The combined $CHCl_3$ extracts were washed with saturated NaCl solution (10 mL), dried ($Na_2SO_4$), filtered, concentrated and further dried under high vacuum to yield a brown oil (1.56 g).

The crude product was purified by column chromatography on silica gel (80 g), eluting with EtOAc-hexane (3:1, v/v) to collect 1-(5-bromo-3-pyridylthio)propan-2-ol ($R_f$ 0.38) (0.05 g). Further elution with MeOH-Et$_3$N (97:3, v/v) afforded a brown oil ($R_f$ 0.58). The oil was dissolved in $CHCl_3$. The $CHCl_3$ solution was dried ($Na_2SO_4$), filtered, concentrated and further dried under high vacuum to yield 1.01 g of (2-(5-bromo(3-pyridylthio))isopropyl) methylamine and (2-(5-bromo(3-pyridylthio))propyl)methylamine as a 56:38 mixture, respectively. The mixture was used without further purification.

(2-(5-Bromo(3-pyridylthio))-isopropyl)methylamine Hemigalactarate and (2-(5-Bromo(3-pyridylthio))propyl)methylamine Hemigalactarate A hot solution of the mixture of (2-(5-bromo(3-pyridylthio))isopropyl)methylamine and (2-(5-bromo(3-pyridylthio))propyl)methylamine (1.01 g, 3.867 mmol) in ethanol (15 mL) was treated in one portion with galactaric acid (0.406 g, 1.937 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (5 mL). The filtrate was diluted with ethanol (22.5 mL). The mixture was allowed to cool to ambient temperature and was allowed to stand for 16 h. The resulting solids were filtered, washed with ethanol (2×5 mL), and vacuum dried at 45° C. to give 0.512 g (36.1%) of light-beige, crystalline flakes, mp 146.5–149.5° C. Analysis indicated a 57:41 mixture of (2-(5-bromo(3-pyridylthio))-isopropyl)methylamine hemigalactarate and (2-(5-bromo(3-pyridylthio))propyl) methylamine hemigalactarate. The compound exhibits a Ki of 5500 nM.

Example 6

Synthesis of 3-(5-Bromo-3-pyridylthio))propyl) methylamine Hemigalactarate 3-(5-Bromo-3-pyridylthio)propan-1-ol Under a nitrogen atmosphere, a mixture of 3-mercapto-1-propanol (3.89 g, 42.21 mmol), sodium hydroxide (1.69 g, 42.21 mmol) and N,N-dimethylformamide (DMF) (40 mL) was heated at 45° C. (oil bath temperature) for 4 h. The resulting solution was cooled to ambient temperature and 3,5-dibromopyridine (8.00 g, 33.77 mmol) was added in one portion. The mixture was stirred and heated at 55° C. (oil bath temperature) for 60 h. The mixture was cooled to ambient temperature, diluted with water (250 mL), treated with saturated NaCl solution and extracted with ether (4×75 mL). The combined ether extracts were washed with saturated NaCl solution (100 mL), dried ($Na_2SO_4$), filtered and concentrated. The residue was dried under high vacuum to give a light-yellow oil (8.25 g). The crude product was purified by vacuum distillation to afford 6.79 g (81.0%) of a very pale-yellow oil, bp 148–152° C. at 0.5 mm Hg.

3-(5-Bromo-3-pyridylthio))propyl)methylamine

Under a nitrogen atmosphere, a cold (0–5° C.), stirring solution of 3-(5-bromo-3-pyridylthio)propan-1-ol (6.64 g, 26.77 mmol) in dichloromethane (35 mL) and triethylamine (35 mL) was treated in one portion with p-toluenesulfonyl chloride (5.36 g, 28.11 mmol). The resulting solution was allowed to warm to ambient temperature and was further stirred for 48 h. The solution was concentrated on a rotary evaporator. The residue was basified at 0–5° C. with saturated $K_2CO_3$ solution (75 mL) and extracted with $CH_2Cl_2$ (4×10 mL). The combined $CH_2Cl_2$ extracts were washed with saturated NaCl solution (100 mL), dried ($Na_2SO_4$), filtered and concentrated (rotary evaporator) to a dark red oil (10.22 g). The oil was transferred to a heavy-walled glass pressure-tube apparatus with methanol (25 mL), and a 40 wt % aqueous solution of methylamine (100 mL) was added. The tube was sealed and the mixture was stirred and heated at 120° C. (oil bath temperature) for 2 h. The resulting solution was allowed to cool to ambient temperature and was further stirred for 16 h. The solution was concentrated on a rotary evaporator. The resulting oil was basified with 1 M NaOH solution (30 mL) and extracted with $CHCl_3$ (5×30 mL). The combined $CHCl_3$ extracts were washed with saturated NaCl solution (50 mL), dried ($Na_2SO_4$), filtered and concentrated to a brown oil. The crude product was purified by column chromatography on silica gel (190 g), eluting with EtOAc-hexane (3:1, v/v) to collect 3-(5-bromo-3-pyridylthio)propan-1-ol ($R_f$ 0.40) (0.46 g). Further elution with MeOH-Et$_3$N (97:3, v/v) afforded 4.52 g (64.6%) of 3-(5-bromo-3-pyridylthio))propyl)methylamine ($R_f$ 0.27) as a light-yellow oil.

3-(5-Bromo-3-pyridylthio))propyl)methylamine Hemigalactarate

A hot solution of 3-(5-bromo-3-pyridylthio))propyl) methylamine (1.00 g, 3.828 mmol) in ethanol (15 mL) was treated in one portion with galactaric acid (0.402 g, 1.914 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (5 mL). The filtrate was diluted with ethanol (22.5 mL). The mixture was allowed to cool to ambient temperature and was further cooled at 5° C. for 16 h. The resulting solids were filtered, washed with ethanol (5 mL), and vacuum dried at 40° C. to give 1.28 g (91.3%) of an off-white, crystalline powder, mp 152.5–154.5.° C. The compound exhibits a Ki of 39950 nM.

Example 7

Synthesis of 2-(3-Pyridyloxy)ethylamine Hemigalactarate

2-Chloro-1-(3-pyridyloxy)ethane

Under a nitrogen atmosphere, a solution of 3-hydroxypyridine (12.00 g, 126.18 mmol) in N,N-dimethylformamide (DMF) (63 mL) was added drop-wise over 25 min to a cold (0–5° C.), stirring slurry of sodium hydride (6.17 g of an 80% dispersion in mineral oil, 205.7 mmol) in DMF (130 mL). The mixture was allowed to stir and warm to ambient temperature over 1 h. Next, 1-bromo-2-chloroethane (21.71 g, 151.37 mmol) was added drop-wise over 45 min. The resulting dark-brown mixture was stirred at ambient temperature for 24 h. Gas chromatographic analysis indicated an incomplete reaction; therefore, more 1-bromo-2-chloroethane (8.65 g, 60.3 mmol) and sodium hydride (2.09 g of an 80% dispersion in mineral oil, 69.7 mmol) were added. The mixture was stirred at ambient temperature for 40 h. Water (60 mL) was carefully added over 30 min, followed by saturated NaCl solution (40 mL), and the mixture was extracted with ether (6×50 mL). The combined orange-yellow ether extracts were washed with saturated NaCl solution (75 mL). The ether layer was dried ($Na_2SO_4$), filtered, and concentrated by rotary evaporation to a residue that was dried briefly under high vacuum to give 2.87 g (14.4%) of a light-brown oil.

2-(3-Pyridyloxy)ethylamine

The 2-chloro-1-(3-pyridyloxy)ethane (1.23 g, 7.80 mmol) was dissolved in methanol (25 mL) and added to concentrated ammonium hydroxide solution (29.7%, 14.8 M, 55 mL) in a heavy-walled glass pressure-tube apparatus. The tube was sealed and the mixture was stirred and heated at 125° C. (oil bath temperature) for 42 h. After cooling, the mixture was concentrated by rotary evaporation. Saturated NaCl solution (10 mL) was added to the residue, and the solution (pH 6) was extracted with ether (3×25 mL) to remove impurities. The aqueous layer was diluted with saturated NaCl solution (15 mL) and basified to pH 12 with 10% NaOH solution (5 mL). The mixture was extracted with chloroform (4×50 mL). The combined light-yellow chloroform extracts were dried ($Na_2SO_4$), filtered, and concentrated by rotary evaporation to a residue that was dried briefly under high vacuum to give 0.390 g (36.2%) of a light-yellow oil.

2-(3-Pyridyloxy)ethylamine Hemigalactarate

To a solution of 2-(3-pyridyloxy)ethylamine (0.390 g, 2.823 mmol) in ethanol (6 mL) was added galactaric acid (0.276 g, 1.312 mmol). Water (1.7 mL) was added drop-wise, while warming the solution to reflux. To remove some white, insoluble solids, the warm solution was filtered through a glass wool plug, washing the filter plug with a warm solution of ethanol-water (4:1, v/v) (1.9 mL). The filtrate was diluted with ethanol (9 mL). The mixture was allowed to cool to ambient temperature and was further cooled at 5° C. for 12 days. The product had precipitated as a semi-crystalline oil. The solvent was removed by rotary evaporation, and the resulting solids were vacuum dried at 40° C. for 24 h. The resulting solids were slurried in 2-propanol, and subsequently diluted with anhydrous ether. The solids were filtered, washed with ether, and vacuum dried at 40° C. for 24 h to give 0.598 g (87.1%) of a fluffy, off-white powder, mp 151–156° C. The compound exhibits a Ki of 1600 nM. The compound exhibits neurotransmitter release of 30 percent.

Example 8

Synthesis of Methyl(2-(3-pyridyloxy)ethyl)amine Hemigalactarate

2-Chloro-1-(3-pyridyloxy)ethane

Under a nitrogen atmosphere, a solution of 3-hydroxypyridine (2.00 g, 21.0 mmol) in N,N-dimethylformamide (DMF) (10 mL) was added drop-wise over 5 min to a cold (0–5° C.), stirring slurry of sodium hydride (0.756 g of an 80% dispersion in mineral oil, 27.5 mmol) in DMF (15 mL). The mixture was allowed to stir and warm to ambient temperature over 1 h. Next, 1-bromo-2-chloroethane (3.60 g, 25.2 mmol) was added drop-wise over 5 min. The resulting dark-brown mixture was stirred at ambient temperature for 4 h. Water (30 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 3.96 g (66.1%) of a light-brown oil.

Methyl(2-(3-pyridyloxy)ethyl)amine

The 2-chloro-1-(3-pyridyloxy)ethane (2.17 g, 13.8 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH was adjusted to 1 with 10% HCl solution and impurities were extracted with chloroform (2×50 mL). The pH of the aqueous phase was raised to 6 with 10% NaOH solution and other impurities were extracted with ether (3×25 mL). The aqueous layer was basified to pH 10 with 10% NaOH solution and extracted with chloroform (4×50 mL). The combined chloroform extracts were dried ($Na_2SO_4$), filtered, and concentrated by rotary evaporation to a residue that was dried briefly under high vacuum to give 0.253 g (12.0%) of an oil.

Methyl(2-(3-pyridyloxy)ethyl)amine Hemigalactarate

To a solution of methyl(2-(3-pyridyloxy)ethyl)amine (0.233 g, 1.53 mmol) in ethanol (4 mL) was added galactaric acid (0.161 g, 0.775 mmol). Water (1 mL) was added drop-wise, while warming the solution to reflux. To remove some white, insoluble solids, the warm solution was filtered through a glass wool plug, washing the filter plug with a warm solution of ethanol-water (4:1, v/v). The filtrate was diluted with ethanol (20 mL). The mixture was allowed to cool to ambient temperature and was further cooled at 5° C. for 48 h. The resulting solids were filtered, washed with cold ethanol (4 mL), and vacuum dried at 40° C. to give 0.307 g (77.9%) of a white to off-white, crystalline powder, mp 148.5–151.5° C. (d). The compound exhibits a Ki of 65 nM; the effect at muscle sites is 0 percent; and the effect at ganglia sites is 0 percent. The compound exhibits neurotransmitter release of 143 percent.

Example 9

Synthesis of Dimethyl(2-(3-pyridyloxy)ethylamine Hemigalactarate

2-Chloro-1-(3-pyridyloxy)ethane

Under a nitrogen atmosphere, a solution of 3-hydroxypyridine (12.00 g, 126.18 mmol) in N,N-dimethylformamide (DMF) (63 mL) was added drop-wise over 25 min to a cold (0–5° C.), stirring slurry of sodium hydride (6.17 g of an 80% dispersion in mineral oil, 205.7 mmol) in DMF (130 mL). The mixture was allowed to stir and warm to ambient temperature over 1 h. Next, 1-bromo-2-chloroethane (21.71 g, 151.37 mmol) was added drop-wise over 45 min. The resulting dark-brown mixture was stirred at ambient temperature for 24 h. Gas chromatographic analysis indicated an incomplete reaction; therefore, more 1-bromo-2-chloroethane (8.65 g, 60.3 mmol) and sodium hydride (2.09 g of an 80% dispersion in mineral oil, 69.7 mmol) were added. The mixture was stirred at ambient temperature for 40 h. Water (60 mL) was carefully added over 30 min, followed by saturated NaCl solution (40 mL), and the mixture was extracted with ether (6×50 mL). The combined orange-yellow ether extracts were washed with saturated NaCl solution (75 mL). The ether layer was dried ($Na_2SO_4$), filtered, and concentrated by rotary evaporation to a residue that was dried briefly under high vacuum to give 2.87 g (14.4%) of a light-brown oil.

Dimethyl(2-(3-pyridyloxy)ethylamine

The 2-chloro-1-(3-pyridyloxy)ethane (2.21 g, 10.41 mmol) was dissolved in methanol (14 mL) and added to a 40 wt % aqueous solution of dimethylamine (22 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (7 mL) and 10% NaOH solution were added to the residue (brown liquid), giving pH 12. The mixture was extracted with chloroform (4×20 mL). The combined chloroform extracts were dried ($Na_2SO_4$), filtered, and concentrated by rotary evaporation to a residue that was dried briefly under high vacuum to give 1.184 g of a brown oil. Further purification was accomplished as follows: The oil was diluted with water (10 mL) and acidified to pH 6 with 10% HCl solution (6 mL). The mixture was extracted with ether (3×25 mL) to remove impurities. The aqueous phase was treated with saturated NaCl solution (15 mL) and basified with 10% NaOH solution to pH 12. The product was extracted with chloroform (4×20 mL). The combined light-yellow chloroform extracts were dried ($Na_2SO_4$), filtered, and concentrated by rotary evaporation to a residue that was dried briefly under high vacuum to give 0.727 g (42.0%) of a light-yellow oil.

Dimethyl(2-(3-pyridyloxy)ethylamine Hemigalactarate

To a solution of dimethyl(2-(3-pyridyloxy)ethylamine (0.727 g, 4.37 mmol) in ethanol (11 mL) was added galactaric acid (0.46 g, 2.19 mmol). Water (3.5 mL) was added drop-wise, while warming the solution to reflux. To remove some white, insoluble solids, the warm solution was filtered through a glass wool plug, washing the filter plug with a warm solution of ethanol-water (4:1, v/v) (3.5 mL). The filtrate was diluted with ethanol (17 mL). The mixture was allowed to cool to ambient temperature and was further cooled at 5° C. for 10 days. Very few solids precipitated. Consequently, the solution was concentrated to a residue that was vacuum dried for 20 h. The solids were slurried in 2-propanol and diluted with anhydrous ether. The precipitate was filtered, washed with ether, and vacuum dried at 40° C. to give 0.818 g (68.9%) of an off-white, slightly beige powder, mp 113–117° C. The compound exhibits a Ki of 151 nM; the effect at muscle sites is 0 percent; and the effect at ganglia sites is 0 percent. The compound exhibits neurotransmitter release of 0 percent.

Example 10

Synthesis of 3-(3-Pyridyloxy)propylamine Hemigalactarate

3-Chloro-1-(3-pyridyloxy)propane

Under a nitrogen atmosphere, a solution of 3-hydroxypyridine (35.00 g, 0.368 mmol) in N,N-dimethylformamide (DMF) (150 mL) was slowly added drop-wise over 15 min to a cold (0–5° C.), stirring slurry of sodium hydride (17.64 g of an 80% dispersion in mineral oil, 0.588 mol) in DMF (250 mL). The mixture was allowed to stir and warm to ambient temperature over 1 h. The gray slurry was cooled to 0–5° C., and 1-chloro-3-iodopropane (90.3 g, 0.442 mol) was added drop-wise over 30 min. The resulting dark-brown mixture was allowed to stir and warm to ambient temperature over 16 h. Water (500 mL) was added and the mixture was divided into equal parts. Each half was diluted with saturated NaCl solution (200 mL) and extracted with ether (5×200 mL). All ether extracts were combined and concentrated to give 55.1 g (87.3%) of a dark-brown oil.

3-(3-Pyridyloxy)propylamine

The 3-chloro-1-(3-pyridyloxy)propane (1.98 g, 11.6 mmol) was dissolved in methanol (25 mL) and added to concentrated ammonium hydroxide solution (29.7%, 14.8 M, 55 mL) in a heavy-walled glass pressure-tube apparatus. The tube was sealed and the mixture was stirred and heated at 100° C. (oil bath temperature) for 6 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 0.354 g (20.1%) of an oil.

3-(3-Pyridyloxy)propylamine Hemigalactarate

To a solution of 3-(3-pyridyloxy)propylamine (0.354 g, 2.30.mmol) in ethanol (5 mL) was added galactaric acid (0.244 g, 1.16 mmol). Water (1.5 mL) was added drop-wise, while warming the solution to reflux. To remove some white, insoluble solids, the warm solution was filtered through a glass wool plug, washing the filter plug with a warm solution of ethanol-water (4:1, v/v). The filtrate was diluted with ethanol (25 mL). The mixture was allowed to cool to ambient temperature and was further cooled at 5° C. for 16 h. The solids were filtered, washed with cold ethanol (5 mL), and vacuum dried at 40° C. to give 344.8 mg (58.3%) of light-yellow crystals, mp 176–178° C. The compound exhibits a Ki of 65 nM; the effect at muscle sites is 0 percent; and the effect at ganglia sites is 0 percent. The compound exhibits a Ki of 12 nM; the effect at muscle sites is 0 percent; and the effect at ganglia sites is 0 percent. The compound exhibits neurotransmitter release of 0 percent.

Example 11

Synthesis of Dimethyl(3-(3-pyridyloxy)propyl)amine Hemigalactarate

3-Chloro-1-(3-pyridyloxy)propane

Under a nitrogen atmosphere, a solution of 3-hydroxypyridine (35.00 g, 0.368 mmol) in N,N-dimethylformamide (DMF) (150 mL) was slowly added drop-wise over 15 min to a cold (0–5° C.), stirring slurry of sodium hydride (17.64 g of an 80% dispersion in mineral oil, 0.588 mol) in DMF (250 mL). The mixture was allowed to stir and warm to ambient temperature over 1 h. The gray slurry was cooled to 0–5° C., and 1-chloro-3-iodopropane (90.3 g, 0.442 mol) was added drop-wise over 30 min. The resulting dark-brown mixture was allowed to stir and warm to ambient temperature over 16 h. Water (500 mL) was added and the mixture was divided into equal parts. Each half was diluted with saturated NaCl solution (200 mL) and extracted with ether (5×200 mL). All ether extracts were combined and concentrated to give 55.1 g (87.3%) of a dark-brown oil.

Dimethyl(3-(3-pyridyloxy)propyl)amine

The 3-chloro-1-(3-pyridyloxy)propane (2.00 g, 11.65 mmol) was dissolved in methanol (25 mL) and added to a 40 wt % aqueous solution of dimethylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and the mixture was extracted with ether (3×25 mL) to remove impurities. The aqueous layer was basified to pH 10 with 10% NaOH solution and extracted with chloroform (4×50 mL). The combined chloroform extracts were dried ($Na_2SO_4$), filtered, and concentrated to give 1.95 g (92.9%) of an oil.

Dimethyl(3-(3-pyridyloxy)propyl)amine Hemigalactarate

To a solution of dimethyl(3-(3-pyridyloxy)propyl)amine (1.95 g, 10.8 mmol) in ethanol (15 mL) was added galactaric acid (0.696 g, 3.30 mmol). Water (4 mL) was added drop-wise, while warming the solution to reflux. To remove some white, insoluble solids, the warm solution was filtered through a glass wool plug, washing the filter plug with a warm solution of ethanol-water (4:1, v/v). The filtrate was diluted with ethanol (80 mL). The mixture was allowed to cool to ambient temperature and was further cooled at 5° C. for 16 h. No solids precipitated. Consequently, the solution was concentrated to a crystalline solid. The solid was slurried in ether, filtered, washed with ether, and vacuum dried at 40° C. to give 1.94 g (62.7%) of brown powdery crystals, mp 137–140° C. The compound exhibits a Ki of 126 nM; the effect at muscle sites is 8 percent; and the effect at ganglia sites is 5 percent. The compound exhibits neurotransmitter release of 32 percent.

Example 12

Synthesis of 4-(3-Pyridyloxy)butylamine Hemigalactarate

4-Chloro-1-(3-pyridyloxy)butane

Under a nitrogen atmosphere, a solution of 3-hydroxypyridine (3.50 g, 36.8 mmol) in N,N-dimethylformamide (DMF) (10 mL) was added drop-wise over 5 min to a cold (0–5° C.), stirring slurry of sodium hydride (1.16 g of an 80% dispersion in mineral oil, 38.6 mmol) in DMF (40 mL). The mixture was allowed to stir and warm to ambient temperature over 1 h. The mixture was then cooled to 0–5° C., and 1-chloro-4-iodobutane (9.67 g, 44.2 mmol) was added drop-wise over 5 min. The resulting dark-brown mixture was stirred at ambient temperature for 2 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 6.89 g (quantitative yield) of an oil.

4-(3-Pyridyloxy)butylamine

The 4-chloro-1-(3-pyridyloxy)butane (2.00 g, 10.8 mmol) was dissolved in methanol (25 mL) and added to concentrated ammonium hydroxide solution (29.7%, 14.8 M, 50 mL) in a heavy-walled glass pressure-tube apparatus. The tube was sealed and the mixture was stirred and heated at 100° C. (oil bath temperature) for 6 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 1.25 g (74.2%) of an oil.

4-(3-Pyridyloxy)butylamine Hemigalactarate

To a solution of 4-(3-pyridyloxy)butylamine (1.25 g, 7.50 mmol) in ethanol (12 mL) was added galactaric acid (0.791 g, 3.76 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (30 mL). The mixture was allowed to cool to ambient temperature and was further cooled at 5° C. for 48 h. Very few solids precipitated. Consequently, the solution was concentrated to a flaky solid. The product was slurried in 2-propanol, and the 2-propanol was decanted. The product was vacuum dried at 40° C. to give 1.28 g (62.7%) of fine, white powder, mp 177–180° C. The compound exhibits a Ki of 232 nM; the effect at muscle sites is 0 percent; and the effect at ganglia sites is 11 percent. The compound exhibits neurotransmitter release of 100 percent.

Example 13

Synthesis of Methyl(4-(3-pyridyloxy)butyl)amine Hemigalactarate

4-Chloro-1-(3-pyridyloxy)butane

Under a nitrogen atmosphere, a solution of 3-hydroxypyridine (3.50 g, 36.8 mmol) in N,N-dimethylformamide (DMF) (10 mL) was added drop-wise over 5 min to a cold (0–5° C.), stirring slurry of sodium hydride (1.16 g of an 80% dispersion in mineral oil, 38.6 mmol) in DMF (40 mL). The mixture was allowed to stir and warm to ambient temperature over 1 h. The mixture was then cooled to 0–5° C., and 1-chloro-4-iodobutane (9.67 g, 44.2 mmol) was added drop-wise over 5 min. The resulting dark-brown mixture was stirred at ambient temperature for 2 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 6.89 g (quantitative yield) of an oil.

Methyl(4-(3-pyridyloxy)butyl)amine

The 4-chloro-1-(3-pyridyloxy)butane (2.00 g, 10.8 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 1.47 g (75.5%) of an oil.

Methyl(4-(3-pyridyloxy)butyl)amine Hemigalactarate

To a solution of methyl(4-(3-pyridyloxy)butyl)amine (1.25 g, 7.50 mmol) in ethanol (15 mL) was added galactaric acid (0.858 g, 4.08 mmol). Water (4 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (40 mL). The mixture was allowed to cool to ambient temperature and was further cooled at 5° C. for 16 h. The solids were filtered, washed with cold ethanol and vacuum dried at 40° C. to give 1.69 g (72.8%) of a fine, white, crystalline powder, mp 173–175° C. The compound exhibits a Ki of 5523 nM. The compound exhibits neurotransmitter release of 56 percent.

Example 14
Synthesis of Dimethyl(4-(3-pyridyloxy)butyl)amine Hemigalactarate
4-Chloro-1-(3-pyridyloxy)butane Under a nitrogen atmosphere, a solution of 3-hydroxypyridine (3.50 g, 36.8 mmol) in N,N-dimethylformamide (DMF) (10 mL) was added drop-wise over 5 min to a cold (0–5° C.), stirring slurry of sodium hydride (1.16 g of an 80% dispersion in mineral oil, 38.6 mmol) in DMF (40 mL). The mixture was allowed to stir and warm to ambient temperature over 1 h. The mixture was then cooled to 0–5° C., and 1-chloro-4-iodobutane (9.67 g, 44.2 mmol) was added drop-wise over 5 min. The resulting dark-brown mixture was stirred at ambient temperature for 2 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 6.89 g (quantitative yield) of an oil.

Dimethyl(4-(3-pyridyloxy)butyl)amine

A portion of the 4-chloro-1-(3-pyridyloxy)butane was dissolved in methanol (25 mL) and added to a 40 wt % aqueous solution of dimethylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 1.26 g of an oil.

Dimethyl(4-(3-pyridyloxy)butyl)amine Hemigalactarate

To a solution of dimethyl(4-(3-pyridyloxy))butylamine (1.26 g, 6.49 mmol) in ethanol (10 mL) was added galactaric acid (0.682 g, 3.25 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (80 mL). The mixture was allowed to cool to ambient temperature and was further cooled at 5° C. for 16 h. Very few solids precipitated. Consequently, the solution was concentrated, and the residue was slurried in ether. The solids were filtered, washed with ether and vacuum dried at 40° C. to give 1.06 g (54.7%) of a light-brown, flaky powder, mp 127–130° C. The compound exhibits a Ki of 3410 nM. The compound exhibits neurotransmitter release of 24 percent.

Example 15
Synthesis of 3-(5-Chloro-3-pyridyloxy)propylamine Hemigalactarate
3-Chloro-5-(3-chloropropoxy)pyridine Under a nitrogen atmosphere, a solution of 5-chloro-3-pyridinol (15.00 g, 115.8 mmol) in N,N-dimethylformamide (DMF) (10 mL) was added drop-wise over 5 min to a cold (0–5° C.), stirring slurry of sodium hydride (3.69 g of an 80% dispersion in mineral oil, 123.0 mmol) in DMF (15 mL). The mixture was allowed to stir and warm to ambient temperature over 1 h. Next, 1-chloro-3-iodopropane (28.4 g, 138.9 mmol) was added drop-wise over 5 min. The resulting dark-brown mixture was stirred at ambient temperature for 4 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 17.22 g (73.0%) of an oil.

3-(5-Chloro-3-pyridyloxy)propylamine

The 3-chloro-5-(3-chloropropoxy)pyridine (5.74 g, 28.0 mmol) was dissolved in methanol (25 mL) and added to concentrated ammonium hydroxide solution (29.7%, 14.8 M, 55 mL) in a heavy-walled glass pressure-tube apparatus. The tube was sealed and the mixture was stirred and heated at 100° C. (oil bath temperature) for 6 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 3.30 g (63.4%) of an oil.

3-(5-Chloro-3-pyridyloxy)propylamine Hemigalactarate

To a solution of 3-(5-chloro-3-pyridyloxy)propylamine (1.00 g, 5.38 mmol) in ethanol (12 mL) was added galactaric acid (0.564 g, 2.688 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (80 mL). The mixture was allowed to cool to ambient temperature and was further cooled at 5° C. for 48 h. No solids had formed. Consequently, the solution was concentrated to a residue that was vacuum dried. The solids were slurried in 2-propanol, and the 2-propanol was evaporated. The resulting solids were slurried in anhydrous ether. The product was filtered, washed with ether and vacuum dried at 40° C. to give 0.996 g (63.5%) of a brown, flaky powder, mp 170–173° C. The compound exhibits a Ki of 46 nM; the effect at muscle sites is 0 percent; and the effect at ganglia sites is 4 percent. The compound exhibits neurotransmitter release of 110 percent.

Example 16
Synthesis of (3-(5-Chloro(3-pyridyloxy))propyl)methylamine Hemigalactarate
3-Chloro-5-(3-chloropropoxy)pyridine Under a nitrogen atmosphere, a solution of 5-chloro-3-pyridinol (15.00 g, 115.8 mmol) in N,N-dimethylformamide (DMF) (10 mL) was added drop-wise over 5 min to a cold (0–5° C.), stirring slurry of sodium hydride (3.69 g of an 80% dispersion in mineral oil, 123.0 mmol) in DMF (15 mL). The mixture was allowed to stir and warm to ambient temperature over 1 h. Next, 1-chloro-3-iodopropane (28.4 g, 138.9 mmol) was added drop-wise over 5 min. The resulting dark-brown mixture was stirred at ambient temperature for 4 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 17.22 g (73.0%) of an oil.

3-(5-Chloro(3-pryridyloxy))propyl)methylamine

The 3-chloro-5-(3-chloropropoxy)pyridine (5.74 g, 28.0 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and impurities were extracted with ether (3×15 mL). The aqueous layer was basified to pH 10 with 10% NaOH solution and extracted with chloroform (4×15 mL). The combined chloroform extracts were dried ($Na_2SO_4$), filtered, and concentrated by rotary evaporation to a residue that was dried briefly under high vacuum to give 4.02 g (71.8%) of an oil.

(3-(5-Chloro(3-pyridyloxy))propyl)methylamine Hemigalactarate

To a solution of (3-(5-chloro(3-pyridyloxy))propyl) methylamine (1.00 g, 5.00 mmol) in ethanol (12 mL) was added galactaric acid (0.791 g, 3.76 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (30 mL). The mixture was allowed to cool to ambient temperature and was further cooled at 5° C. for 48 h. The solids were filtered, washed and vacuum dried at 40° C. to give 1.163 g (76.3%) of off-white, powdery crystals, mp 173–174° C. The compound exhibits a Ki of 11 nM; the effect at muscle sites is 16 percent; and the effect at ganglia sites is 7 percent. The compound exhibits neurotransmitter release of 100 percent.

Example 17

Synthesis of Methyl(3-(5-methoxy-3-pyridyloxy)propyl) amine Hemigalactarate

5-Bromo-3-methoxypyridine

This compound was prepared in 64.7% yield as a white, crystalline powder (mp 28–30° C.) using the general procedure of D. L. Comins and M. O. Killpack, *J. Org. Chem.* 55:69–73 (1990).

5-Methoxy-3-pyridylamine

Crude 5-bromo-3-methoxypyridine (3.50 g, 18.62 mmol) was dissolved in methanol (50 mL) and added to concentrated ammonium hydroxide (29.7%, 14.8 M, 50 mL) and copper(I) bromide (2.67 g, 18.62 mmol) in a heavy-walled glass pressure-tube apparatus. The tube was flushed with nitrogen and sealed. The mixture Was stirred and heated at 170–172° C. (oil bath temperature) for 24 h. After cooling, the solution was concentrated by rotary evaporation to a gummy residue. The residue was diluted with sodium carbonate solution (17.6%, 200 mL) and extracted with $CH_2Cl_2$ (4×50 mL). The combined $CH_2Cl_2$ extracts were dried ($MgSO_4$), filtered, and concentrated by rotary evaporation to give 1.26 g of a cream-brown solid. The aqueous phase was re-extracted with $CH_2Cl_2$ (4×50 mL). The combined $CH_2Cl_2$ extracts were similarly dried and concentrated to give an additional 0.34 g of a cream-brown solid, bringing the total yield to 1.60 g (69.2%).

5-Methoxypyridin-3-ol

A mixture of concentrated sulfuric acid (18 M, 2.83 mL), water (3.84 mL) and crushed ice (6.60 g) was added to 5-methoxy-3-pyridylamine (1.64 g, 13.23 mmol). The cold mixture (0–5° C.) was stirred for 10 min and a solution of sodium nitrite (0.91 g, 13.23 mmol) in water (2.7 mL) was then added. After stirring for 10 min, a boiling solution of concentrated sulfuric acid (8.6 mL) and water (6.6 mL) was added. The mixture was heated until all solids dissolved. Ice (5.0 g) was added to cool the solution. The pH was adjusted to 8 with 10% NaOH solution. Saturated NaCl solution (100 mL) was added, and the mixture was extracted with ethyl acetate (4×100 mL). The combined ethyl acetate extracts were dried ($MgSO_4$), filtered and concentrated by rotary evaporation to give 0.50 g (30.1%) of a brown oil.

5-(3-Chloropropoxy)-3-methoxypyridine

Under a nitrogen atmosphere, a solution of 5-methoxypyridin-3-ol (0.50 g, 4.01 mmol) in DMF (10 mL) was slowly added over 10 min to a cold (0–5° C.), stirring slurry of sodium hydride (0.19 g of an 80% dispersion in mineral oil, 6.33 mmol) in DMF (15 mL). The mixture was allowed to warm to ambient temperature and further stirred for 1 h. To this slurry was added drop-wise over 5 min, 1-chloro-3-iodopropane (0.98 g, 4.81 mmol), and the resulting dark brown mixture was stirred at ambient temperature for 4 h. Cold water (25 mL) was carefully added, followed by saturated NaCl solution (25 mL). The resulting mixture was extracted with ether (4×50 mL). The combined ether extracts were dried ($MgSO_4$), filtered, and concentrated by rotary evaporation producing a dark-brown oil (0.75 g, 92.8%).

Methyl(3-(5-methoxy-3-pyridyloxy)propyl)amine

Crude 5-(3-chloropropoxy)-3-methoxypyridine (0.75 g, 3.73 mmol) was dissolved in methanol (10.5 mL) and added to a 40 wt % aqueous solution of methylamine (10.6 mL) in a heavy-walled glass pressure-tube apparatus. The tube was sealed and the mixture was stirred and heated at 100° C. (oil bath temperature) for 4 h. After cooling, the solution was concentrated by rotary evaporation. Saturated NaCl solution (50 mL) was added, and the mixture was basified with 10% NaOH solution to pH 11. The mixture was extracted with ether (4×50 mL). The combined ether extracts were dried ($MgSO_4$), filtered and concentrated by rotary evaporation to give 0.54 g of a brown oil. The product was purified by column chromatography on silica gel (18 g) eluting with $CHCl_3$—$CH_3OH$ (1:1, v/v) to remove impurities, followed by $CHCl_3$—$CH_3OH$-$Et_3N$ (50:50:2, v/v/v) to collect the product. Selected fractions containing the product were combined and concentrated by rotary evaporation. The resulting brown oil was dissolved in $CHCl_3$ (25 mL), dried ($MgSO_4$), filtered, and concentrated by rotary evaporation to give 0.228 g (31.2%) of a brown oil.

Methyl(3-(5-methoxy-3-pyridyloxy)propyl)amine Hemigalactarate

To a solution of methyl(3-(5-methoxy-3-pyridyloxy) propyl)amine (0.228 g, 1.16 mmol) in ethanol (4.3 mL) was added galactaric acid (122.0 mg, 0.58 mmol). Water (1.2 mL) was added drop-wise, while warming the solution to near reflux. To remove some white, insoluble crystals, the warm solution was filtered through a glass wool plug, washing the filter plug with a warm solution of ethanol-water (4:1, v/v) (1.4 mL). The filtrate was diluted with ethanol (6.5 mL), producing a white precipitate. The mixture was allowed to cool to ambient temperature and was further cooled at 5° C. for 48 h. The precipitate was filtered, washed with ethanol (10 mL), and vacuum dried at 40° C. for 24 h to give 141.2 mg (80.7%) of a white, crystalline solid, mp 140–141° C. The compound exhibits a Ki of 15 nM; the effect at muscle sites is 10 percent; and the effect at ganglia sites is 5 percent. The compound exhibits neurotransmitter release of 54 percent.

Example 18

Synthesis of Methyl(3-(5-isopropoxy-3-pyridyloxy)propyl) amine Monogalactarate

5-Bromo-3-isopropoxypyridine

Potassium metal (6.59 g, 168.84 mmol) was dissolved in dry 2-propanol (60.0 mL) under nitrogen. The resulting potassium isopropoxide was heated with 3,5-dibromopyridine (20.00 g, 84.42 mmol) and copper powder (1 g, 5% by weight of 3,5-dibromopyridine) at 140° C. (oil bath temperature) in a sealed glass tube for 14 h. The reaction mixture was cooled to ambient temperature and extracted with diethyl ether (4×200 mL). The combined ether extracts were dried over sodium sulfate, filtered, and concentrated by rotary evaporation. The crude product obtained was purified by column chromatography over aluminum oxide, eluting with ethyl acetate-hexane (1:9, v/v). Selected fractions were combined and concentrated by rotary evaporation, producing a pale-yellow oil (12.99 g, 71.2%).

5-Isopropoxy-3-pyridylamine

Crude 5-bromo-3-isopropoxypyridine (3.71 g, 17.18 mmol) was dissolved in methanol (46 mL) and added to concentrated ammonium hydroxide (29.7%, 14.8 M, 50 mL) and copper(I) bromide (2.46 g, 17.18 mmol) in a heavy-walled glass pressure-tube apparatus. The tube was sealed and the mixture was stirred and heated at 170° C. (oil bath temperature) for 24 h. After cooling, the solution was concentrated by rotary evaporation. Sodium carbonate solution (17.6%, 200 mL) was added, and the mixture was extracted with $CH_2Cl_2$ (4×50 mL). The combined $CH_2Cl_2$ extracts were dried ($MgSO_4$), filtered, and concentrated by rotary evaporation to give 1.88 g (72.0%) of a brown oil.

5-Isopropoxypyridin-3-ol

A mixture of concentrated sulfuric acid (18 M, 2.64 mL), water (3.59 mL) and crushed ice (6.20 g) was added to 5-isopropoxy-3-pyridylamine (1.88 g, 12.38 mmol). The cold mixture (0–5° C.) was stirred for 10 min and a solution of sodium nitrite (0.85 g, 12.38 mmol) in water (2.5 mL) was then added. After stirring for 10 min, a boiling solution of concentrated sulfuric acid (8.0 mL) and water (6.2 mL) was added. The mixture was heated until all solids dissolved. Ice (5.0 g) was added to cool the solution. The pH was adjusted to 8 with 10% NaOH solution. Saturated NaCl solution (100 mL) was added, and the mixture was extracted with ethyl acetate (4×100 mL). The combined ethyl acetate extracts were dried ($MgSO_4$), filtered and concentrated by rotary evaporation to give 1.69 g (89.4%) of a brown oil.

5-(3-Chloropropoxy)-3-isopropoxypyridine

Under a nitrogen atmosphere, a solution of 5-isopropoxypyridin-3-ol (1.04 g, 6.80 mmol) in DMF (10 mL) was slowly added over 10 min to a cold (0–5° C.), stirring slurry of sodium hydride (0.25 g of an 80% dispersion in mineral oil, 8.33 mmol) in DMF (15 mL). The mixture was allowed to warm to ambient temperature and further stirred for 1 h. To this slurry was added drop-wise over 5 min, 1-chloro-3-iodopropane (1.67 g, 8.16 mmol), and the resulting dark brown mixture was stirred at ambient temperature for 4 h. Cold water (25 mL) was carefully added, followed by saturated NaCl solution (25 mL). The resulting mixture was extracted with ether (4×50 mL). The combined ether extracts were dried ($MgSO_4$), filtered, and concentrated by rotary evaporation producing a dark-brown oil (0.92 g, 59.0%).

Methyl(3-(5-isopropoxy-3-pyridyloxy)propyl)amine

Crude 5-(3-chloropropoxy)-3-isopropoxypyridine (0.92 g, 4.01 mmol) was dissolved in methanol (10 mL) and added to a 40 wt % aqueous solution of methylamine (10 mL) in a heavy-walled glass pressure-tube apparatus. The tube was sealed and the mixture was stirred and heated at 100° C. (oil bath temperature) for 4 h. After cooling, the solution was concentrated by rotary evaporation. Saturated NaCl solution (50 mL) was added, and the mixture was basified with 10% NaOH solution to pH 11. The mixture was extracted with ether (4×50 mL). The combined ether extracts were dried ($MgSO_4$), filtered and concentrated by rotary evaporation to give 1.98 g of a brown oil. The product was purified by column chromatography on silica gel (60 g) eluting with hexane to remove impurities, followed by $CHCl_3$—$CH_3OH$—$Et_3N$ (50:50:2, v/v/v) to collect the product. Selected fractions containing the product were combined and concentrated by rotary evaporation. The resulting brown oil was dissolved in $CHCl_3$ (25 mL), dried ($MgSO_4$), filtered, and concentrated by rotary evaporation to give 0.64 g (71.6%) of a brown oil.

Methyl(3-(5-isopropoxy-3-pyridyloxy)propyl)amine Monogalactarate

To a solution of methyl(3-(5-isopropoxy-3-pyridyloxy) propyl)amine (0.643 g, 2.87 mmol) in ethanol (10.7 mL) was added galactaric acid (302.0 mg, 1.44 mmol). Water (3.0 mL) was added drop-wise, while warming the solution to near reflux. To remove some white, insoluble crystals, the warm solution was filtered through a glass wool plug, washing the filter plug with a warm solution of ethanol-water (4:1, v/v) (3.4 mL). The filtrate was diluted with ethanol (16 mL), producing a white precipitate. The mixture was allowed to cool to ambient temperature and was further cooled at 5° C. for 48 h. The precipitate was filtered, washed with ethanol (10 mL), and vacuum dried at 40° C. for 24 h to give 251.1 mg (53.2%) of a white, crystalline solid, mp 118–120° C. The compound exhibits a Ki of 21 nM; the effect at muscle sites is 22 percent; and the effect at ganglia sites is 0 percent. The compound exhibits neurotransmitter release of 36 percent.

Example 19

Synthesis of Methyl(3-(5-(phenylmethoxy)(3-pyridyloxy)) propyl)amine Hemigalactarate 5-Bromo-3-(phenylmethoxy)pyridine Under a nitrogen atmosphere, small pieces of sodium (1.48 g, 64.4 mmol) were added to benzyl alcohol (17.11 g, 158 mmol), and the mixture was stirred and heated at 70° C. for 18 h. To the stirring, viscous mixture was added 3,5-dibromopyridine (5.00 g, 21.1 mmol), copper powder (0.255 g, 4.0 mmol) and benzyl alcohol (15 mL). The mixture was further heated at 100° C. for 48 h. The reaction mixture was allowed to cool to ambient temperature, diluted with water (50 mL), and extracted with ethyl ether (5×50 mL). The combined ether layers were dried ($Na_2SO_4$), filtered, and concentrated. Distillation at 68–72° C. and 2.6 mm Hg removed excess benzyl alcohol. The remaining yellowish, brown residue was purified by vacuum distillation at 0.05 mm Hg to yield 3.17 g (38.0%) of a white, crystalline solid, mp 64–66° C.

5-(Phenylmethoxy)-3-pyridylamine

A thick-walled glass pressure tube was charged with copper(II) sulfate pentahydrate (1.96 g, 7.85 mmol), 5-bromo-3-(phenylmethoxy)pyridine (4.00 g, 15.15 mmol) and concentrated aqueous ammonia (29.7%, 14.8 M, 37 mL). The tube was sealed and the dark blue suspension was stirred and heated at ~180° C. (oil bath temperature) for 24 h. The mixture was allowed to cool to ambient temperature. After further cooling in an ice-water bath, the mixture was concentrated on a rotary evaporator to a small volume (~20 mL) of a dark-blue solution. The solution was diluted with water (40 mL) and saturated $K_2CO_3$ solution (40 mL) and extracted with $CHCl_3$ (4×40 mL). The combined, turbid-brown $CHCl_3$ extracts were washed with saturated NaCl solution (2×100 ml), dried ($Na_2SO_4$), filtered and concentrated (rotary evaporator). The resulting dark-brown oil, was briefly dried on the vacuum pump to give a dark-brown solid (2.06 g). The product was purified by column chromatography on silica gel (100 g) eluting with $CHCl_3$—MeOH (3:1,v/v). Selected fractions, based on TLC ($R_f$ 0.65) analysis, were combined and concentrated to give a 1.64 g(54.1%) of a tan-brown solid.

5-(Phenylmethoxy)pyridin-3-ol

The 5-(phenylmethoxy)-3-pyridylamine (1.61 g, 8.00 mmol) was stirred into concentrated sulfuric acid (1.7 mL), water (2.5 mL) and ice (4 g). This mixture was allowed to stir for 10 min until the solution became homogeneous. To this cold, stirring solution was added a solution of sodium nitrite (552 mg, 8.00 mmol) in water (2 mL). The mixture was allowed to stir for 10 min. A boiling solution of concentrated sulfuric acid (5 mL) and water (4 mL) was added. The mixture was heated until all solids dissolved. Ice was added to cool the reaction. The pH was adjusted to 8 with 10% NaOH solution and saturated NaCl solution was added. The product was extracted with ethyl acetate (4×100 mL). The combined ethyl acetate extracts were dried ($Na_2SO_4$), filtered, concentrated by rotary evaporation and briefly vacuum to give 1.52 g (94.4%).

5-(3-Chloropropoxy)-3-(phenylmethoxy)pyridine

Under a nitrogen atmosphere, a solution of 5-(phenylmethoxy)pyridine-3-ol (1.52 g, 7.56 mmol) in N,N-dimethylformamide (DMF) (10 mL) was added drop-wise over 5 min to a cold (0–5° C.), stirring slurry of sodium hydride (0.238 g of an 80% dispersion in mineral oil, 7.94 mmol) in DMF (15 mL). The mixture was allowed to stir and warm to ambient temperature over 1 h. Next, 1-chloro-3-iodopropane (1.85 g, 9.07 mmol) was added drop-wise over 5 min. The resulting dark-brown mixture was stirred at ambient temperature for 4 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give an oil.

Methyl(3-(5-(phenylmethoxy)(3-pyridyloxy))propyl)amine

The 5-(3-chloropropoxy)-3-(phenylmethoxy)pyridine (1.52 g, 5.49 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and impurities were extracted with ether (3×15 mL). The aqueous layer was basified to pH 10 with 10% NaOH solution and extracted with chloroform (4×15 mL). The combined chloroform extracts were dried ($Na_2SO_4$), filtered, and concentrated by rotary evaporation to a residue that was dried briefly under high vacuum to give 1.07 g (71.7%) of an oil.

Methyl(3-(5-(phenylmethoxy)(3-pyridyloxy))propyl)amine Hemigalactarate

To a solution of methyl(3-(5-(phenylmethoxy)(3-pyridyloxy))propyl)amine (1.07 g, 3.929 mmol) in ethanol (15 mL) was added galactaric acid (0.413 g, 1.964 mmol). Water (1.5 mL) was added drop-wise, while warming the solution to reflux. To remove some white, insoluble solids, the warm solution was filtered through a glass wool plug, washing the filter plug with a warm solution of ethanol-water (4:1, v/v) (5 mL). The filtrate was diluted with ethanol (23 mL). The mixture was allowed to cool to ambient temperature; however, no solids precipitated. The solution was concentrated by rotary evaporation and briefly dried under high vacuum. The resulting brown solids were dissolved in a mixture of hot 2-propanol (~15 mL) and water (0.8 mL); the dark-brown solution was allowed to cool to ambient temperature. After 30 min of precipitation, the batch was diluted with 2-propanol (30 mL) and stored at 5° C. for 16 h. The resulting solids were filtered, washed with cold 2-propanol (3×5 mL) and vacuum dried at 45° C. to give 0.967 g (65.2%) of a beige powder, mp 137–140° C. The compound exhibits a Ki of 2 nM; the effect at muscle sites is 1 percent; and the effect at ganglia sites is 3 percent. The compound exhibits neurotransmitter release of 38 percent.

Example 20

Synthesis of Methyl(3-(6-methyl(3-pyridyloxy))propyl) amine Hemigalactarate

3-Chloro-1-(6-methyl(3-pyridyloxy))propane

Under a nitrogen atmosphere, a solution of 5-hydroxy-2-methylpyridine (2.00 g, 18.3 mmol) in N,N-dimethylformamide (DMF) (10 mL) was added drop-wise over 5 min to a cold (0–5° C.), stirring slurry of sodium hydride (0.825 g of an 80% dispersion in mineral oil, 27.5 mmol) in DMF (15 mL). The mixture was allowed to stir and warm to ambient temperature over 1 h. Next, 1-chloro-3-iodopropane (4.49 g, 22.0 mmol) was added drop-wise over 5 min. The resulting dark-brown mixture was stirred at ambient temperature for 4 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 4.57 g of an oil.

Methyl(3-(6-methyl(3-pyridyloxy))propyl)amine

The 3-chloro-1-(6-methyl(3-pyridyloxy))propane (2.78 g, 18.3 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH was adjusted to 1 with 10% HCl solution and impurities were extracted with chloroform (4×25 mL). The pH of the aqueous phase was raised to 7 with 10% NaOH solution and other impurities were extracted with ether (4×30 mL). The aqueous layer was basified to pH 11 with 10% NaOH solution and extracted with ether (4×50 mL). The combined ether extracts were dried ($Na_2SO_4$), filtered, and concentrated by rotary evaporation to a residue that was dried briefly under high vacuum to give 1.224 g (45.3%) of an oil.

Methyl(3-(6-methyl(3-pyridyloxy))propyl)amine Hemigalactarate

To a solution of methyl(3-(6-methyl(3-pyridyloxy)) propyl)amine (1.224 g, 6.80 mmol) in ethanol (15 mL) was added galactaric acid (0.714 g, 3.40 mmol). Water (4 mL) was added drop-wise, while warming the solution to reflux. To remove some white, insoluble solids, the warm solution was filtered through a glass wool plug, washing the filter plug with a warm solution of ethanol-water (4:1, v/v). The filtrate was diluted with ethanol (20 mL). The mixture was allowed to cool to ambient temperature and was further cooled at 5° C. for 72 h. The resulting solids were filtered, washed with cold ethanol, and vacuum dried at 40° C. to give 1.596 g (82.3%) of a white, fluffy crystalline powder, mp 152–155° C. The compound exhibits a Ki of 12 nM; and the effect at muscle sites is 0 percent. The compound exhibits neurotransmitter release of 77 percent.

Example 21

Synthesis of Methyl(3-(2-methyl(3-pyridyloxy))propyl) amine Hemigalactarate

3-Chloro-1-(2-methyl(3-pyridyloxy))propane

Under a nitrogen atmosphere, a solution of 3-hydroxy-2-methylpyridine (2.00 g, 18.3 mmol) in N,N-dimethylformamide (DMF) (10 mL) was added drop-wise over 5 min to a cold (0–5° C.), stirring slurry of sodium hydride (0.576 g of an 80% dispersion in mineral oil, 19.2 mmol) in DMF (40 mL). The mixture was allowed to stir and warm to ambient temperature over 1 h. The slurry was cooled to 0–5° C., and 1-chloro-3-iodopropane (4.49 g, 22.0 mmol) was added drop-wise over 5 min. The resulting dark-brown mixture was stirred at ambient temperature for 2 h. Cold water (25 mL) was added, followed by saturated NaCl solution (25 mL), and the mixture was extracted with ether (4×100 mL). The combined ether extracts were dried (Na$_2$SO$_4$), filtered, and concentrated by rotary evaporation to a residue that was dried briefly under high vacuum to give 3.25 g (96.2%) of an oil.

Methyl(3-(2-methyl(3-pyridyloxy))propyl)amine

The 3-chloro-1-(2-methyl(3-pyridyloxy))propane (2.00 g, 10.8 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and the mixture was extracted with ether (3×25 mL) to remove impurities. The aqueous layer was basified to pH 10 with 10% NaOH solution and extracted with chloroform (4×50 mL). The combined chloroform extracts were dried (Na$_2$SO$_4$), filtered, and concentrated to give 1.19 g (61.0%) of an oil.

Methyl(3-(2-methyl(3-pyridyloxy))propyl)amine Hemigalactarate

To a solution of methyl(3-(2-methyl(3-pyridyloxy))propyl)amine (1.19 g, 6.61 mmol) in ethanol (12 mL) was added galactaric acid (0.696 g, 3.30 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (30 mL). The mixture was allowed to cool to ambient temperature and was further cooled at 5° C. for 48 h. No solids precipitated. Consequently, the solution was concentrated to a flaky solid. The solid was slurried in 2-propanol, filtered, washed with 2-propanol, and vacuum dried at 40° C. to give 1.37 g (72.8%) of an off-white, flaky powder, mp 145–148° C. The compound exhibits a Ki of 236 nM; the effect at muscle sites is 0 percent; and the effect at ganglia sites is 15 percent. The compound exhibits neurotransmitter release of 69 percent.

Example 22

Ethyl(3-(3-pyridyloxy)propyl)amine Hemigalactarate
3-Chloro-1-(3-pyridyloxy)propane Under a nitrogen atmosphere, a solution of 3-hydroxypyridine (35.00 g, 0.368 mmol) in N,N-dimethylformamide (DMF) (150 mL) was slowly added drop-wise over 15 min to a cold (0–5° C.), stirring slurry of sodium hydride (17.64 g of an 80% dispersion in mineral oil, 0.588 mol) in DMF (250 mL). The mixture was allowed to stir and warm to ambient temperature over 1 h. The gray slurry was cooled to 0–5° C., and 1-chloro-3-iodopropane (90.3 g, 0.442 mol) was added drop-wise over 30 min. The resulting dark-brown mixture was allowed to stir and warm to ambient temperature over 16 h. Water (500 mL) was added and the mixture was divided into equal parts. Each half was diluted with saturated NaCl solution (200 mL) and extracted with ether (5×200 mL). All ether extracts were combined and concentrated to give 55.1 g (87.3%) of a dark-brown oil.

Ethyl(3-(3-pyridyloxy)propyl)amine

The 3-chloro-1-(3-pyridyloxy)propane (1.00 g, 5.84 mmol) was dissolved in methanol (50 mL) and added to a 2.0 M solution of ethylamine in tetrahydrofuran (5 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and impurities were extracted with ether (3×15 mL). The aqueous layer was basified to pH 10 with 10% NaOH solution and extracted with chloroform (4×15 mL). The combined chloroform extracts were dried (Na$_2$SO$_4$), filtered, and concentrated by rotary evaporation to a residue that was dried briefly under high vacuum to give 400 mg (38.1%) of an oil.

Ethyl(3-(3-pyridyloxy)propyl)amine Hemigalactarate

To a solution of ethyl(3-(3-pyridyloxy)propyl)amine (400 mg, 2.20 mmol) in ethanol (11 mL) was added galactaric acid (233 mg, 1.10 mmol). Water (3.5 mL) was added drop-wise, while warming the solution to reflux. To remove some white, insoluble solids, the warm solution was filtered through a glass wool plug, washing the filter plug with a warm solution of ethanol-water (4:1, v/v) (3.5 mL). The filtrate was diluted with ethanol (17 mL). The mixture was allowed to cool to ambient temperature and was further cooled at 5° C. Very few solids precipitated. Consequently, the solution was concentrated to a residue that was vacuum dried. The solids were slurried in 2-propanol, and the 2-propanol was evaporated. The resulting solids were slurried in anhydrous ether. The product was filtered, washed with ether, and vacuum dried at 40° C. to give 348 mg (55.0%) of a brown, flaky powder, mp 147–150° C. The compound exhibits a Ki of 66 nM; the effect at muscle sites is 13 percent; and the effect at ganglia sites is 13 percent. The compound exhibits neurotransmitter release of 57 percent.

Example 23

Synthesis of (Methylethyl)(3-(3-pyridyloxy)propyl)amine
3-Chloro-1-(3-pyridyloxy)propane Under a nitrogen atmosphere, a solution of 3-hydroxypyridine (35.00 g, 0.368 mmol) in N,N-dimethylformamide (DMF) (150 mL) was slowly added drop-wise over 15 min to a cold (0–5° C.), stirring slurry of sodium hydride (17.64 g of an 80% dispersion in mineral oil, 0.588 mol) in DMF (250 mL). The mixture was allowed to stir and warm to ambient temperature over 1 h. The gray slurry was cooled to 0–5° C., and 1-chloro-3-iodopropane (90.3 g, 0.442 mol) was added drop-wise over 30 min. The resulting dark-brown mixture was allowed to stir and warm to ambient temperature over 16 h. Water (500 mL) was added and the mixture was divided into equal parts. Each half was diluted with saturated NaCl solution (200 mL) and extracted with ether (5×200 mL). All ether extracts were combined and concentrated to give 55.1 g (87.3%) of a dark-brown oil.

(Methylethyl)(3-(3-pyridyloxy)propyl)amine

The 3-chloro-1-(3-pyridyloxy)propane (0.80 g, 4.66 mmol) was dissolved in methanol (25 mL) and added to diisopropylamine (25 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 0.531 g (58.6%) of a dark-brown oil. The compound exhibits a Ki of 8500 nM. The compound exhibits neurotransmitter release of 16 percent.

Example 24
Synthesis of Benzyl(3-(3-pyridyloxy)propyl)amine
3-Chloro-1-(3-pyridyloxy)propane Under a nitrogen atmosphere, a solution of 3-hydroxypyridine (35.00 g, 0.368 mmol) in N,N-dimethylformamide (DMF) (150 mL) was slowly added drop-wise over 15 min to a cold (0–5° C.), stirring slurry of sodium hydride (17.64 g of an 80% dispersion in mineral oil, 0.588 mol) in DMF (250 mL). The mixture was allowed to stir and warm to ambient temperature over 1 h. The gray slurry was cooled to 0–5° C., and 1-chloro-3-iodopropane (90.3 g, 0.442 mol) was added drop-wise over 30 min. The resulting dark-brown mixture was allowed to stir and warm to ambient temperature over 16 h. Water (500 mL) was added and the mixture was divided into equal parts. Each half was diluted with saturated NaCl solution (200 mL) and extracted with ether (5×200 mL). All ether extracts were combined and concentrated to give 55.1 g (87.3%) of a dark-brown oil.

Benzyl(3-(3-pyridyloxy)propyl)amine

The 3-chloro-1-(3-pyridyloxy)propane (0.65 g, 3.78 mmol) was dissolved in methanol (20 mL) and added to a mixture of benzylamine (13.5 mL) in water (20 mL) in a heavy-walled glass pressure-tube apparatus. The tube was sealed and the mixture was stirred and heated at 120° C. (oil bath temperature) for 3 h. After cooling, the mixture was concentrated by rotary evaporation, and saturated NaCl solution (25 mL) was added to the residue. The mixture was acidified to pH 1 with 10% HCl solution and extracted with $CHCl_3$ (2×35 mL) to remove impurities. The aqueous phase was basified to pH 10 with 10% NaOH solution, and the mixture was extracted with chloroform (4×50 mL). The combined chloroform extracts were dried ($MgSO_4$), filtered, and concentrated by rotary evaporation to a residue that was dried briefly under high vacuum to give a brown oil. The oil was concentrated by vacuum distillation to remove excess benzylamine (bp 85° C. at 15 mm Hg). The remaining residue (0.483 g) was purified by column chromatography on silica gel (25 g) eluting with $CH_3OH$—$NH_4OH$ (50:1, v/v). Fractions containing the product ($R_f$ 0.39) were combined and concentrated on a rotary evaporator. The residue was re-chromatographed on silica gel (10 g). Fractions containing the product were combined and concentrated on a rotary evaporator. The residue was dissolved in $CHCl_3$ and the $CHCl_3$ solution was dried ($MgSO_4$), filtered, and concentrated by rotary evaporation to a residue that was dried briefly under high vacuum to give 20 mg (2.2%) of a light-brown oil. The compound exhibits a Ki of 3000 nM. The compound exhibits neurotransmitter release of 29 percent.

Example 25
Synthesis of Cyclopropyl(3-(3-pyridyloxy)propyl)amine Hemigalactarate
3-Chloro-1-(3-pyridyloxy)propane Under a nitrogen atmosphere, a solution of 3-hydroxypyridine (35.00 g, 0.368 mmol) in N,N-dimethylformamide (DMF) (150 mL) was slowly added drop-wise over 15 min to a cold (0–5° C.), stirring slurry of sodium hydride (17.64 g of an 80% dispersion in mineral oil, 0.588 mol) in DMF (250 mL). The mixture was allowed to stir and warm to ambient temperature over 1 h. The gray slurry was cooled to 0–5° C., and 1-chloro-3-iodopropane (90.3 g, 0.442 mol) was added drop-wise over 30 min. The resulting dark-brown mixture was allowed to stir and warm to ambient temperature over 16 h. Water (500 mL) was added and the mixture was divided into equal parts. Each half was diluted with saturated NaCl solution (200 mL) and extracted with ether (5×200 mL). All ether extracts were combined and concentrated to give 55.1 g (87.3%) of a dark-brown oil.

Cyclopropyl(3-(3-pyridyloxy)propyl)amine

An Ace Glass pressure tube (185 mL) was charged with 3-chloro-1-(3-pyridyloxy)propane (0.762 g, 4.437 mmol), cyclopropylamine (8.24 g, 194.3 mmol), water (20 mL) and methanol (20 mL). The resulting light-brown solution was heated at 120° C. (oil bath temperature) for 2.5 h and allowed to cool to ambient temperature over 16 h. The solution was concentrated by rotary evaporation to an oily residue that was diluted with saturated NaCl solution (25 mL). The mixture was acidified to pH 1.0 with 10% HCl solution and extracted with $CHCl_3$ (2×35 mL) to remove impurities. The aqueous phase was basified to pH 6 with 10% NaOH solution and extracted (4×25 mL) to remove other impurities. The aqueous phase was basified to pH 10 with 10% NaOH solution and extracted with $CHCl_3$ (4×50 mL). The combined $CHCl_3$ extracts were dried ($Na_2SO_4$), filtered, concentrated (rotary evaporator) and briefly dried under high vacuum to give 0.250 g of a brown oil. The oil was purified by column chromatography on silica gel (20 g) eluting with $CHCl_3$—$CH_3OH$ (100:2) to remove impurities, followed by $CHCl_3$—$CH_3OH$-$Et_3N$ (50:50:2) to remove the product. Selected fractions were combined to give 220 mg (25.8%) of a brown semi-solid.

Cyclopropyl(3-(3-pyridyloxy)propyl)amine Hemigalactarate

To a solution of cyclopropyl(3-(3-pyridyloxy)propyl) amine (0.239 g, 1.244 mmol) in ethanol (4 mL) was added galactaric acid (130.7 mg, 622 mmol). Water (1.0 mL) was added drop-wise, while warming the solution to near reflux. To remove some white, insoluble crystals, the warm solution was filtered through a glass wool plug, washing the filter plug with a warm solution of ethanol-water (4:1, v/v) (1 mL). The filtrate was diluted with ethanol (6 mL), cooled to ambient temperature and kept at 5° C. for 24 h. Crystallization did not occur. Consequently, the solution was concentrated by rotary evaporation to a brown, glassy residue. The residue was dissolved in 2-propanol containing a few drops of water, and the solution was concentrated to a syrup. The syrup was slurried in a mixture of 2-propanol-diethyl ether, producing a somewhat powdery solid. The solvents were evaporated on a rotary evaporator, and the resulting solids were slurried in a mixture of 2-propanol-diethyl ether. The mixture was stored at 5° C. for 24 h. The solvent was decanted; the tan solids were washed with ether (3×5 mL), decanting the wash each time. The tan solids were dried under a stream of nitrogen and under high vacuum to give 0.246 g (66.5%) of a light-beige powder, mp 124–130° C. The compound exhibits a Ki of 165 nM; the effect at muscle sites is 9 percent; and the effect at ganglia sites is 10 percent. The compound exhibits neurotransmitter release of 51 percent.

Example 26
Synthesis of Methyl(1-methyl-3-(3-pyridyloxy)propyl) amine Hemigalactarate
3-Bromo-1-(3-pyridyloxy)butane Under a nitrogen atmosphere, a solution of 3-hydroxypyridine (1.00 g, 10.52 mmol) in N,N- dimethylformamide (DMF) (10 mL) was slowly added to a cold (0° C.), stirring slurry of sodium hydride (0.50 g of an 60% dispersion in mineral oil, 12.63 mmol) in DMF (5 mL). After stirring 30 min, 1,3-dibromobutane (2.50 g, 11.57 mmol) was slowly added drop-wise. The resulting mixture was stirred at 0–4° C. for 16 h. Cold water (10 mL) was added, and the mixture was extracted with ether (3×100 mL). The combined ether extracts were dried (Na$_2$SO$_4$), filtered and concentrated by rotary evaporation to give 2.23 g (92.5%) of an oil.

Methyl(1-methyl-3-(3-pyridyloxy)propyl)amine

Crude 3-bromo-1-(3-pyridyloxy)butane (2.00 g, 8.69 mmol) from the previous step was dissolved in methanol (10 mL) and added to a 40 wt % aqueous solution of methylamine (30 mL) in a heavy-walled glass pressure-tube apparatus. The mixture was stirred and heated at 100° C. (oil bath temperature) for 16 h. After cooling, the mixture was concentrated by rotary evaporation, and the product was extracted with chloroform (4×50 mL). The combined chloroform extracts were dried (Na$_2$SO$_4$), filtered and concentrated by rotary evaporation to give 1.25 g of a pale-yellow oil. Purification by vacuum distillation yielded 0.94 g (60.3%) of a colorless oil, bp 65–67° C. at 0.5 mm Hg.

Methyl(1-methyl-3-(3-pyridyloxy)propyl)amine Hemigalactarate

To a solution of methyl(1-methyl-3-(3-pyridyloxy) propyl)amine (0.92 g, 5.11 mmol) in ethanol (25 mL) at 70° C. was added galactaric acid (0.537 g, 2.55 mmol). Water (0.5 mL) was added drop-wise, while stirring producing a clear solution. Some white, insoluble solids were removed by filtration. The filtrate was concentrated to 15 mL, and was allowed to cool to ambient temperature. After standing for 16 h, the precipitate was filtered, washed with ether (10 mL) and vacuum dried at 45° C. for 18 h to give 1.15 g (78.9%) of an off-white, amorphous powder, mp 134–136° C. The compound exhibits a Ki of 138 nM; the effect at muscle sites is 16 percent; and the effect at ganglia sites is 20 percent. The compound exhibits neurotransmitter release of 49 percent.

Example 27

Synthesis of (3-(5-Chloro(3-pyridyloxy))-1-methylpropyl) methylamine Hemigalactarate 3-Bromo-1-(5-chloro(3-pyridyloxy)butane Under a nitrogen atmosphere, a solution of 5-chloro-3-hydroxypyridine (1.00 g, 7.72 mmol) in N,N-dimethylformamide (DMF) (10 mL) was slowly added to a cold (0° C.), stirring slurry of sodium hydride (0.40 g of an 60% dispersion in mineral oil, 11.58 mmol) in DMF (5 mL). After stirring 30 min, 1,3-dibromobutane (1.83 g, 8.49 mmol) was added drop-wise. The resulting mixture was stirred at 0° C. for 14 h. Cold water (10 mL) was added, and the mixture was extracted with ether (3×100 mL). The combined ether extracts were dried (Na$_2$SO$_4$), filtered and concentrated by rotary evaporation to give 1.80 g (88.5%) of pale-yellow oil.

(3-(5-Chloro(3-pyridyloxy))-1-methylpropyl)methylamine

Crude 3-bromo-1-(5-chloro(3-pyridyloxy)butane (1.50 g, 5.67 mmol) from the previous step was dissolved in methanol (10 mL) and added to a 40 wt % aqueous solution of methylamine (40 mL) in a heavy-walled glass pressure-tube apparatus. The mixture was stirred and heated at 100° C. (oil bath temperature) for 14 h. After cooling, the mixture was concentrated by rotary evaporation, and the product was extracted with chloroform (3×100 mL). The combined chloroform extracts were dried (Na$_2$SO$_4$), filtered, and concentrated by rotary evaporation to give a pale-brown oil. The product was dissolved in cold, 15% aqueous HCl (15 mL), stirred at 0° C. for 45 min and extracted with chloroform (50 mL). The aqueous layer was cooled to 0° C., basified with 15% aqueous NaOH solution to pH 8–9 and extracted with chloroform (3×75 mL). The combined extracts were dried (Na$_2$SO$_4$), filtered and concentrated by rotary evaporation to give 0.929 g (76.6%) of a pale-yellow oil.

(3-(5-Chloro(3-pyridyloxy))-1-methylpropyl)methylamine Hemigalactarate

To a solution of (3-(5-chloro(3-pyridyloxy))-1-methylpropyl)methylamine (0.70 g, 3.27 mmol) in ethanol (20 mL) at 70° C. was added galactaric acid (0.343 g, 1.63 mmol). Water (0.5 mL) was added drop-wise while stirring, producing a clear solution. Some white, insoluble solids were removed by filtration. The filtrate was concentrated to 10 mL and was allowed to cool to ambient temperature. After standing 16 h, the precipitate was filtered, washed with ether (10 mL) and vacuum dried at 45° C. for 24 h to give 0.775 g (74.3%) of a light-beige, amorphous powder, mp 155–157° C. The compound exhibits a Ki of 1601 nM. The compound exhibits neurotransmitter release of 30 percent.

Example 28

Synthesis of Methyl(3-(3-nitrophenoxy)propyl)amine Hemigalactarate 1-(3-Chloropropoxy)-3-nitrobenzene Under a nitrogen atmosphere, a solution of 3-nitrophenol (15.00 g, 108.0 mmol) in N,N-dimethylformamide (DMF) (10 mL) was added drop-wise over 5 min to a cold (0–5° C.), stirring slurry of sodium hydride (3.42 g of an 80% dispersion in mineral oil, 114.0 mmol) in DMF (40 mL). The mixture was allowed to stir and warm to ambient temperature over 1 h. The mixture was cooled to 0–5° C., and 1-chloro-3-iodopropane (26.37 g, 127.0 mmol) was added drop-wise over 5 min. The resulting dark-brown mixture was stirred at ambient temperature for 2 h. Water (25 mL) was added, followed by saturated NaCl solution (25 mL), and the mixture was extracted with ether (4×50 mL). The combined ether extracts were dried (Na$_2$SO$_4$), filtered, and concentrated by rotary evaporation to a residue that was dried briefly under high vacuum to give 19.75 g (85.1%) of an oil.

Methyl(3-(3-nitrophenoxy)propyl)amine

The 1-(3-chloropropoxy)-3-nitrobenzene (1.00 g, 4.65 mmol) was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and impurities were extracted with ether (3×15 mL). The aqueous layer was basified to pH 10 with 10% NaOH solution and extracted with chloroform (4×15 mL). The combined chloroform extracts were dried (Na$_2$SO$_4$), filtered, and concentrated by rotary evaporation to a residue that was dried briefly under high vacuum to give 493 mg (50.6%) of an oil.

Methyl(3-(3-nitrophenoxy)propyl)amine Hemigalactarate

To a solution of methyl(3-(3-nitrophenoxy)propyl)amine (493 mg, 2.35 mmol) in ethanol (10 mL) was added galactaric acid (247 mg, 1.17 mmol). Water (3.0 mL) was added drop-wise, while warming the solution to near reflux. To remove some white, insoluble crystals, the warm solution was filtered through a glass wool plug, washing the filter plug with a warm solution of ethanol-water (4:1, v/v). The filtrate was diluted with ethanol (15 mL), producing a white precipitate. The mixture was allowed to cool to ambient temperature and was further cooled at 5° C. The precipitate was filtered, washed with ethanol (10 mL), and vacuum dried at 40° C. for 24 h to give 617 mg (83.5%) of white, fluffy, crystals, mp 186–187° C. The compound exhibits a Ki of 392 nM; the effect at muscle sites is 10 percent; and the effect at ganglia sites is 9 percent. The compound exhibits neurotransmitter release of 67 percent.

Example 29

Synthesis of 1-(3-Chloropropoxy)-3-nitrobenzene Hemigalactarate 1-(3-Chloropropoxy)-3-nitrobenzene Under a nitrogen atmosphere, a solution of 3-nitrophenol (15.00 g, 108.0 mmol) in N,N-dimethylformamide (DMF) (10 mL) was added drop-wise over 5 min to a cold (0–5° C.), stirring slurry of sodium hydride (3.42 g of an 80% dispersion in mineral oil, 114.0 mmol) in DMF (40 mL). The mixture was allowed to stir and warm to ambient temperature over 1 h. The mixture was cooled to 0–5° C., and 1-chloro-3-iodopropane (26.37 g, 127.0 mmol) was added drop-wise over 5 min. The resulting dark-brown mixture was stirred at ambient temperature for 2 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 19.75 g (85.1%) of an oil.

3-(3-Chloropropoxy)phenylamine

Under a nitrogen atmosphere, a solution of 1-(3-chloropropoxy)-3-nitrobenzene (7.90 g, 36.64 mmol) in ethanol was added to 10% palladium on carbon in a Parr hydrogenation bottle. The mixture was hydrogenated on a Parr shaker. Because of very little hydrogen uptake, Raney® nickel (50% slurry in water) was carefully added to the reaction mixture and hydrogenation continued. When hydrogenation was complete the mixture was filtered through a mat of Celite® filter aid. The filtrate was concentrated on a rotary evaporator to an oil.

3-(3-Aminopropoxy)phenylamine

The 3-(3-chloropropoxy)phenylamine (1.98 g, 11.6 mmol) was dissolved in methanol (25 mL) and added to concentrated ammonium hydroxide solution (29.7%, 14.8 M, 50 mL) in a heavy-walled glass pressure-tube apparatus. The tube was sealed and the mixture was stirred and heated at 100° C. (oil bath temperature) for 6 h. After cooling, the mixture was concentrated by rotary evaporation. Saturated NaCl solution (10 mL) was added to the residue, and the solution (pH 6) was extracted with ether (3×25 mL) to remove impurities. The aqueous layer was basified to pH 10 with 10% NaOH solution, and the mixture was extracted with chloroform (4×25 mL). The combined chloroform extracts were dried ($Na_2SO_4$), filtered, and concentrated by rotary evaporation to a residue that was dried briefly under high vacuum to give 1.37 g of an oil.

3-(3-Aminopropoxy)phenylamine Hemigalactarate

To a solution of 3-(3-aminopropoxy)phenylamine (1.37 g, 8.25 mmol) in ethanol (12 mL) was added galactaric acid (0.867 g, 4.13 mmol). Water (3 mL) was added drop-wise, while warming the solution to reflux. To remove some white, insoluble solids, the warm solution was filtered through a glass wool plug, washing the filter plug with a warm solution of ethanol-water (4:1, v/v) (4 mL). The filtrate was diluted with ethanol (80 mL). The mixture was allowed to cool to ambient temperature and was further cooled at 5° C. No solids had formed. Consequently, the solution was concentrated to a residue that was vacuum dried. The solids were slurried in hot 2-propanol and cooled to ambient temperature. The product was filtered, washed with 2-propanol and vacuum dried at 40° C. to give 1.462 g (65.4%) of a beige, crystalline powder, mp 182–185° C. The compound exhibits a Ki of 442 nM. The compound exhibits neurotransmitter release of 14 percent.

Example 30

Synthesis of (3-(3-Aminophenoxy)propyl)methylamine Hemigalactarate 1-(3-Chloropropoxy)-3-nitrobenzene Under a nitrogen atmosphere, a solution of 3-nitrophenol (15.00 g, 108.0 mmol) in N,N-dimethylformamide (DMF) (10 mL) was added drop-wise over 5 min to a cold (0–5° C.), stirring slurry of sodium hydride (3.42 g of an 80% dispersion in mineral oil, 114.0 mmol) in DMF (40 mL). The mixture was allowed to stir and warm to ambient temperature over 1 h. The mixture was cooled to 0–5° C., and 1-chloro-3-iodopropane (26.37 g, 127.0 mmol) was added drop-wise over 5 min. The resulting dark-brown mixture was stirred at ambient temperature for 2 h. Water (25 mL) was added, followed by saturated NaCl solution (25 mL), and the mixture was extracted with ether (4×50 mL). The combined ether extracts were dried ($Na_2SO_4$), filtered, and concentrated by rotary evaporation to a residue that was dried briefly under high vacuum to give 19.75 g (85.1%) of an oil.

3-(3-Chloropropoxy)phenylamine

Under a nitrogen atmosphere, a solution of 1-(3-chloropropoxy)-3-nitrobenzene (7.90 g, 36.64 mmol) in ethanol was added to 10% palladium on carbon in a Parr hydrogenation bottle. The mixture was hydrogenated on a Parr shaker. Because of very little hydrogen uptake, Raney® nickel (50% slurry in water) was carefully added to the reaction mixture and hydrogenation continued. When hydrogenation was complete the mixture was filtered through a mat of Celite® filter aid. The filtrate was concentrated on a rotary evaporator to an oil.

(3-(3-Aminophenoxy)propyl)methylamine

The 3-(3-chloropropoxy)phenylamine was dissolved in methanol (25 mL) and added to a 40 wt % aqueous solution of methylamine (50 mL) in a heavy-walled glass pressure-tube apparatus. The tube was sealed and the mixture was stirred and heated at 100° C. (oil bath temperature) for 4 h. After cooling, the mixture was concentrated by rotary evaporation. Saturated NaCl solution (25 mL) was added to the residue. The pH of the solution was adjusted to 6, and impurities were extracted with ether (4×30 mL). The aqueous layer was basified to pH 11 with 10% NaOH solution and extracted with chloroform (4×50 mL). The combined chloroform extracts were dried ($Na_2SO_4$), filtered, and concentrated by rotary evaporation to a residue that was dried briefly under high vacuum to give 2.77 g of an oil.

(3-(3-Aminophenoxy)propyl)methylamine Hemigalactarate

To a solution of (3-(3-aminophenoxy)propyl)methylamine (2.77 g, 15.30 mmol) in ethanol was added galactaric acid (1.61 g, 7.65 mmol). Water was added drop-wise, while warming the solution to reflux. To remove some white, insoluble solids, the warm solution was filtered through a glass wool plug, washing the filter plug with a warm solution of ethanol-water (4:1, v/v). The filtrate was diluted with ethanol. The mixture was allowed to cool to ambient temperature and was further cooled at 5° C. No solids had formed. Consequently, the solution was concentrated to a residue that was vacuum dried. The solids were slurried in 2-propanol, and the 2-propanol was evaporated. The resulting solids were slurried in anhydrous ether. The product was filtered, washed with ether and vacuum dried at 40° C. to give 3.928 g (89.6%) of brown, powdery crystals, mp 160–170° C. The compound exhibits a Ki of 64 nM; the effect at muscle sites is 11 percent; and the effect at ganglia sites is 5 percent. The compound exhibits neurotransmitter release of 30 percent. The compound exhibits neurotransmitter release of 60 percent.

Example 31

Synthesis of Dimethyl(3-(3-(methylamino)propoxy)phenyl) amine Hemigalactarate
(3-(3-Chloropropoxy)phenyl)dimethylamine Under a nitrogen atmosphere, a solution of 3-(dimethylamino)phenol (3.50 g, 25.51 mmol) in DMF (30 mL) was slowly added over 10 min to a cold (0–5° C.), stirring slurry of sodium hydride (0.80 g of an 80% dispersion in mineral oil, 26.79 mmol) in DMF (40 mL). The mixture was allowed to warm to ambient temperature and further stirred for 1.25 h. The resulting brown mixture was cooled to 0–5C. To this slurry was added drop-wise over 5 min, 1-chloro-3-iodopropane (6.26 g, 30.62 mmol). The resulting reddish brown mixture was stirred at ambient temperature for 4.25 h. Cold water (35 mL) was carefully added, followed by saturated NaCl solution (35 mL). The resulting mixture was extracted with ether (4×50 mL). The combined dull-yellow ether extracts were dried ($Na_2SO_4$), filtered, and concentrated by rotary evaporation producing a light-brown oil (5.65 g).

Dimethyl(3-(3-(methylamino)propoxy)phenyl)amine

The crude (3-(3-chloropropoxy)phenyl)dimethylamine (4.06 g, 19.01 mmol) was dissolved in methanol (30 mL) and added to a 40 wt % aqueous solution of methylamine (75 mL) in a heavy-walled glass pressure-tube apparatus. The tube was sealed and the mixture was stirred at ambient temperature for 16 h, followed by heating at 87° C. (oil bath temperature) for 3 h. After cooling, the solution was concentrated by rotary evaporation to a lavender-brown semisolid. Saturated NaCl solution (35 mL) was added. The mixture was acidified to pH 1 with 10% HCl solution and extracted with $CHCl_3$ (5×30 mL) to remove impurities. The dark-brown aqueous layer was basified to pH 7 with 30% NaOH solution and extracted with ether (4×40 mL) to remove impurities. The brown aqueous layer was basified with 30% NaOH solution to pH 12 and extracted with ether (4×50 mL). The combined ether extracts were dried ($Na_2SO_4$), filtered and concentrated by rotary evaporation, producing an oil. The product was dried briefly under high vacuum to afford 2.24 g (56.6%) of a dark-brown oil.

Dimethyl(3-(3-(methylamino)propoxy)phenyl)amine Hemigalactarate

To a solution of dimethyl(3-(3-(methylamino)propoxy) phenyl)amine (2.23 g, 10.71 mmol) in ethanol (34 mL) was added galactaric acid (1.13 g, 5.35 mmol). Water (4.8 mL) was added drop-wise, while warming the solution to near reflux. To remove some white, insoluble crystals, the warm solution was filtered through a glass wool plug, washing the filter plug with a warm solution of ethanol-water (4:1, v/v) (10 mL). The filtrate was diluted with ethanol (50 mL), producing a precipitate. The mixture was allowed to cool to ambient temperature and was further cooled at 5° C. for 16 h. The precipitate was filtered, washed with ethanol (3×10 mL) and vacuum dried at 40° C. for 48 h to give 2.95 g (87.9%) of a fluffy, light-gray to off-white powder, mp 159.5–162.5° C. (d). The compound exhibits a Ki of 10000 nM. The compound exhibits neurotransmitter release of 16 percent.

Example 32

Synthesis of Methyl(3-tricyclo[7.3.1.0<5,13>]tridec-2-yloxypropyl)amine Hemigalactarate
3-Chloro-1-tricyclo[7.3.1.0<5,13>tridec-2-yloxypropane Under a nitrogen atmosphere, a solution of 8-hydroxyjulolidine (tetrahydro-1H,5H-benzo[ij]quinolizin-8-ol) (2.00 g, 10.57 mmol) in DMF (15 mL) was slowly added over 5 min to a cold (0–5° C.), stirring slurry of sodium hydride (0.38 g of an 80% dispersion in mineral oil, 12.67 mmol) in DMF (15 mL). The mixture was allowed to warm to ambient temperature and further stirred for 1 h. To this slurry was added drop-wise over 5 min, 1-chloro-3-iodopropane (2.59 g, 12.67 mmol), and the resulting brown mixture was stirred at ambient temperature for 4 h. Cold water (25 mL) was carefully added, followed by saturated NaCl solution (25 mL). The resulting mixture was extracted with ether (4×50 mL). The combined ether extracts were dried ($MgSO_4$), filtered, concentrated by rotary evaporation to a residue that was dried briefly under high vacuum producing 1.90 g (67.6%) of an oil.

Methyl(3-tricyclo[7.3.1.0<5,13>]tridec-2-yloxypropyl) amine

Crude 3-chloro-1-tricyclo[7.3.1.0<5,13>tridec-2-yloxypropane (1.90 g, 7.15 mmol) was dissolved in methanol (25 mL) and added to a 40 wt % aqueous solution of methylamine (20 mL) in a heavy-walled glass pressure-tube apparatus. The tube was sealed and the mixture was stirred and heated at 100° C. (oil bath temperature) for 4 h. After cooling, the solution was concentrated by rotary evaporation, and saturated NaCl solution (50 mL) was added. The mixture was extracted with ether (4×50 mL). The combined ether extracts were dried ($MgSO_4$), filtered and concentrated by rotary evaporation to give a residue (2.60 g). The residue was purified by column chromatography on silica gel (60 g) eluting with $CHCl_3$—$CH_3OH$ (1:1, v/v) to remove impurities, followed by $CHCl_3$—$CH_3OH$-$Et_3N$ (50:50:2, v/v/v) to collect the product. Selected fractions containing the product were combined and concentrated by rotary evaporation to afford 1.694 g (91.0%) of material.

Methyl(3-tricyclo[7.3.1.0<5.13>]tridec-2-yloxypropyl) amine Hemigalactarate

To a solution of methyl(3-tricyclo[7.3. 1.0<5,13>]tridec-2-yloxypropyl)amine (1.694 g, 6.51 mmol) in ethanol (23 mL) was added galactaric acid (0.656 g, 3.12 mmol). Water (6.6 mL) was added drop-wise, while warming the solution to near reflux. Upon cooling the mixture to ambient temperature, the resulting precipitate was filtered. The solids were collected and dissolved in a mixture of methanol (50 mL) and water (75 mL), while warming the solution to near reflux. The warm solution was filtered to remove a few insoluble solids and cooled. However, crystallization did not occur. The solution was concentrated, and the resulting solids were recrystallized from ethanol-water. After cooling at 5° C. for 48 h, the precipitate was filtered, washed with ethanol and vacuum dried at 40° C. for 16 h to give 0.699 g (29.4%) of a yellow, crystalline solid, mp 169–171° C. The compound exhibits a Ki of 100000 nM.

Example 33

Synthesis of (3-(3-Methoxyphenoxy)propyl)methylamine
3-Chloro-1-(3-methoxyphenoxy)propane Under a nitrogen atmosphere, a solution of 3-methoxyphenol (2.00 g, 16.11 mmol) in DMF (10 mL) was slowly added over 5 min to a cold (0–5° C.), stirring slurry of sodium hydride (0.70 g of an 80% dispersion in mineral oil, 23.33 mmol) in DMF (15 mL). The mixture was allowed to warm to ambient temperature and further stirred for 1 h. To this slurry was added drop-wise over 5 min, 1-chloro-3-iodopropane (3.95 g, 19.32 mmol), and the resulting brown mixture was stirred at ambient temperature for 4 h. Cold water (25 mL) was carefully added, followed by saturated NaCl solution (25 mL). The resulting mixture was extracted with ether (4×50 mL). The combined ether extracts were dried ($MgSO_4$), filtered, concentrated by rotary evaporation to a residue that was dried briefly under high vacuum producing a light-brown oil (3.27 g, quantitative yield).

(3-(3-Methoxyphenoxy)propyl)methylamine

Crude 3-chloro-1-(3-methoxyphenoxy)propane (1.27 g, 6.33 mmol) was dissolved in methanol (25 mL) and added to a 40 wt % aqueous solution of methylamine (25 mL) in a heavy-walled glass pressure-tube apparatus. The tube was sealed and the mixture was stirred and heated at 100° C. (oil bath temperature) for 4 h. After cooling, the solution was concentrated by rotary evaporation, and saturated NaCl solution (50 mL) was added. The mixture was acidified to pH 1 with 10% HCl solution, and extracted with $CHCl_3$ (4×25 mL) to remove impurities. The pH of the aqueous phase was adjusted to 7 with 10% NaOH solution, and the mixture was extracted with ether (4×30 mL) to remove impurities. The aqueous phase was basified with 10% NaOH solution to pH 11. The mixture was extracted with ether (4×50 mL). The combined ether extracts were dried ($MgSO_4$), filtered and concentrated by rotary evaporation to give a residue. The residue was briefly dried under high vacuum producing a light-brown oil (0.11 g). The oil was purified by column chromatography on silica gel (10 g) eluting with $CHCl_3$—$CH_3OH$ (1:1, v/v) to remove impurities, followed by $CHCl_3$—$CH_3OH$-$Et_3N$ (50:50:2, v/v/v) to collect the product ($R_f$ 0.27). Selected fractions containing the product were combined and concentrated by rotary evaporation. The resulting brown oil was dissolved in $CHCl_3$, and the $CHCl_3$ solution was dried ($MgSO_4$), filtered and concentrated by rotary evaporation to a residue. The residue was dried briefly under vacuum to give 0.021 g (1.7%) of a light-brown oil. The compound exhibits a Ki of 5300 nM.

Example 34

Synthesis of (3-Benzo[3,4-d]1,3-dioxolan-5-yloxypropyl) methylamine Hemigalactarate 1-Benzo[3,4-d]1,3-dioxolan-5-yloxy-3-chloropropane Under a nitrogen atmosphere, a solution of sesamol (2.00 g, 14.48 mmol) in DMF (15 mL) was slowly added over 5 min to a cold (0–5° C.), stirring slurry of sodium hydride (0.65 g of an 80% dispersion in mineral oil, 21.67 mmol) in DMF (10 mL). The mixture was allowed to warm to ambient temperature and further stirred for 1 h. To this slurry was added drop-wise over 5 min, 1-chloro-3-iodopropane (3.55 g, 1 7.37 mmol), and the resulting brown mixture was stirred at ambient temperature for 4 h. Cold water (25 mL) was carefully added, followed by saturated NaCl solution (25 mL). The resulting mixture was extracted with ether (4×50 mL). The combined ether extracts were dried ($MgSO_4$), filtered, concentrated by rotary evaporation to a residue that was dried briefly under high vacuum producing a brown oil.

(3-Benzo[3,4-d]1,3-dioxolan-5-yloxypropyl)methylamine

Crude 1-benzo[3,4-d]1,3-dioxolan-5-yloxy-3-chloropropane (1.95 g, 9.1 mmol) was dissolved in methanol (25 mL) and added to a 40 wt % aqueous solution of methylamine (25 mL) in a heavy-walled glass pressure-tube apparatus. The tube was sealed and the mixture was stirred and heated at 100° C. (oil bath temperature) for 4 h. After cooling, the solution was concentrated by rotary evaporation, and saturated NaCl solution (50 mL) was added. The mixture was acidified to pH 1 with 10% HCl solution, and extracted with $CHCl_3$ (4×25 mL) to remove impurities. The pH of the aqueous phase was adjusted to 7 with 10% NaOH solution, and the mixture was extracted with ether (4×30 mL) to remove impurities. The aqueous phase was basified with 10% NaOH solution to pH 11. The mixture was extracted with ether (4×50 mL). The combined ether extracts were dried ($MgSO_4$), filtered and concentrated by rotary evaporation to give a residue. The residue was briefly dried under high vacuum producing a light-brown oil (0.286 g). The oil was purified by column chromatography on silica gel (20 g) eluting with $CHCl_3$—$CH_3OH$ (1:1, v/v) to remove impurities, followed by $CHCl_3$—$CH_3OH$-$Et_3N$ (50:50:2, v/v/v) to collect the product ($R_f$ 0.14). Selected fractions containing the product were combined and concentrated by rotary evaporation. The resulting brown oil was dissolved in $CHCl_3$ and the $CHCl_3$ solution was dried ($MgSO_4$), filtered and concentrated by rotary evaporation to a residue. The residue was dried under vacuum at 40° C. to give 0.274 g (14.4%) of a brown oil.

(3-Benzo[3,4-d]1,3-dioxolan-5-yloxypropyl)methylamine Hemigalactarate

To a solution of (3-benzo[3,4-d]1,3-dioxolan-5-yloxypropyl)methylamine (0.252 g, 1.21 mmol) in ethanol (6 mL) was added galactaric acid (140.0 mg, 0.67 mmol). Water (1.5 mL) was added drop-wise, while warming the solution to near reflux. To remove some white, insoluble crystals, the warm solution was filtered through a glass wool plug, washing the filter plug with a warm solution of ethanol-water (4:1, v/v) (1.5 mL). The filtrate was diluted with ethanol (7.5 mL). The mixture was allowed to cool to ambient temperature and was further cooled at 5° C. for 48 h. The precipitate was filtered, washed with ether, and vacuum dried at 40° C. for 16 h to give 301 mg (79.4%) of a white, crystalline solid, mp 158–160° C. The compound exhibits a Ki of 16600 nM. The compound exhibits neurotransmitter release of 41 percent.

Example 35

Synthesis of 3-(4-Piperidinyloxy)pyridine dihydrochloride

N-(tert-Butoxycarbonyl)-piperidin-4-one

This compound was prepared as light-yellow, crystalline plates, mp 71–73.5° C. (literature mp 74–75°) using the general procedure of P. Houghton and G. R. Humphrey, European Patent Application No. 0470668 A1 (Merck Sharp and Dohme, Inc.).

N-(tert-Butoxycarbonyl)-piperidin-4-ol

A mixture of N-(tert-butoxycarbonyl)-piperidin-4-one (4.90 g, 24.59 mmol), sodium borohydride (1.52 g, 40.18 mmol) and methanol was stirred for 10 h. The solvent was removed by rotary evaporation. The residue was treated with portions of acetone (4×20 mL) and evaporated each time on a rotary evaporator. Water (10 mL) was added and the product was extracted with $CHCl_3$ (4×20 mL). The combined $CHCl_3$ extracts were dried ($K_2CO_3$), filtered and concentrated to afford 3.80 g (76.8%) of a thick syrup, that solidified upon standing.

3-(N-(tert-Butoxycarbonyl)-4-piperidinyloxy)pyridine

Under a nitrogen atmosphere, a cold (0–5° C.), stirring solution of N-(tert-butoxycarbonyl)-piperidin-4-ol (800 mg, 3.98 mmol), 3-hydroxypyridine (378 mg, 3.98 mmol) and triphenylphosphine (1.148 g, 4.38 mmol) in dry tetrahydrofuran (20 mL) was treated drop-wise via syringe with diethyl azodicarboxylate (0.75 mL, 830 mg, 4.76 mmol). The mixture was allowed to stir and warm to ambient temperature over 16 h. The solvent was removed by rotary evaporation, and the crude product was purified by column chromatography over silica gel, eluting with hexane-ethyl acetate-(9:1, v/v). Selected fractions were collected and concentrated to produce 800 mg (72%) of a thick syrup.

3-(4-Piperidinyloxy)pyridine

A cold (0–5° C.), stirring solution of 3-(N-(tert-butoxycarbonyl)-4-piperidinyloxy)pyridine (500 mg, 1.796 mmol) in anisole (8 mL) was treated with trifluoroacetic acid (8 mL, 11.84 g, 103.8 mmol). The resulting solution was stirred for 30 min. The volatiles were removed on a rotary evaporator, and the residue was neutralized and basified to pH 9 with solid $K_2CO_3$ and water. The mixture was extracted with chloroform (4×20 mL). The combined chloroform extracts were dried ($K_2CO_3$), filtered and concentrated. The crude product was purified by column chromatography over silica gel, eluting with chloroform-acetone (9:1, v/v). Selected fractions were collected and concentrated to give 260 mg (81.2%) of an off-white, viscous liquid.

3-(4-Piperidinyloxy)pyridine Dihydrochloride

Concentrated HCl (2 mL) was added to 3-(4-piperidinyloxy)pyridine (260 mg, 1.459 mmol), and the resulting solution was concentrated by rotary evaporation. Ethanol was added to the residue and removed by rotary evaporation to dry the product. The procedure was repeated several times until a solid was obtained. The resulting material was recrystallized from 2-propanol. The solids were filtered and dried under vacuum to afford 233 mg (63.7%) of an off-white solid, mp 152–155° C. The compound exhibits a Ki of 592 nM; the effect at muscle sites is 16 percent; and the effect at ganglia sites is 9 percent.

Example 36

Synthesis of 3-((3S)-3-Pyrrolidinyloxy)pyridine dihydrochloride (3R)-N-(tert-Butoxycarbonyl)-3-hydroxypyrrolidine Under a nitrogen atmosphere, di-tert-butyl dicarbonate (12.53 g, 57.39 mmol) was slowly added in portions to a cold (0–5° C.), stirring solution of (R)-(+)-3-pyrrolidinol (5.00 g, 57.39 mmol) in tetrahydrofuran (30 mL). The light yellow solution was allowed to stir and warm to ambient temperature over several hours. The solution was concentrated (rotary evaporation and high vacuum) to give a yellow oil. The oil was treated with saturated $NaHCO_3$ solution (100 mL) and extracted with EtOAc (3×75 mL). The combined EtOAc extracts were dried ($Na_2SO_4$), filtered, concentrated by rotary evaporation and vacuum dried to give a yellow oil containing colorless crystals. The product was recrystallized from EtOAc-cyclohexane (~1:1–1:2). The mixture was cooled at 5° C. for 16 h. The off-white crystals were filtered, washed with cyclohexane (2×5 mL) and vacuum dried at 40° C. for 16 h affording 7.36 g (68.5%) of off-white, slightly yellow crystals, mp 62.5–65.5° C., literature mp 62–65° C. (P. G. Houghton et al., *J. Chem. Soc. Perkin Trans* 1 (Issue 13): 1421–1424 (1993), $[\alpha]^{20.5}_D$ −25.0° (c 1.0, $CH_2Cl_2$), literature $[\alpha]_D$ −22.7° (c 1.0, $CH_2Cl_2$). The crystallization liquors were concentrated, and the syrup was cooled at 5° C. The resulting yellow crystals were filtered, washed with cyclohexane and vacuum dried at 40° C. producing an additional 2.98 g of a yellow powder, mp 60.5–62.5° C. bringing the total yield to 10.34 g (96.2%).

3-((3S)-N-(tert-Butoxycarbonyl)-3-pyrrolidinyloxy)pyridine

Under a nitrogen atmosphere, diethyl azodicarboxylate (4.65 g, 26.70 mmol) was added to a cold (0–5° C.), stirring solution of triphenylphosphine (7.00 g, 26.70 mmol) in dry tetrahydrofuran (60 mL, distilled from sodium and benzophenone). The mixture was stirred at 0–5° C. for 15 min. The resulting yellow solution was treated drop-wise at 0–5° C. with a solution of (3R)-N-(tert-butoxycarbonyl)-3-hydroxypyrrolidine (2.50 g, 13.35 mmol) in dry THF (20 mL) producing a thick yellow mixture. At 0–5° C., 3-hydroxypyridine (2.54 g, 26.70 mmol) was added in one portion. The resulting yellow solution was allowed to stir and warm to ambient temperature over 24 h. The solution was diluted with $CH_2Cl_2$ (150 mL) and washed with saturated $K_2CO_3$ solution (2×100 mL). The combined $CH_2Cl_2$ extracts were dried ($Na_2SO_4$), filtered, concentrated by rotary evaporation and briefly dried under high vacuum to give a viscous, light-yellow gel. The crude product was purified by column chromatography on silica gel (302 g), eluting with $CHCl_3$—$CH_3OH$ (95:5, v/v). Selected fractions containing the product ($R_f$ 0.44) were combined and concentrated to afford 2.50 g of a light-yellow oil, that contained solids. Impure fractions were combined and concentrated to give 16 g of solids. The solids were triturated with pentane (4×75 mL) in an ultrasonic bath, and the pentane filtrate was concentrated to give 3.40 g of an oil. The oil was chromatographed on silica gel (180 g), eluting with $CHCl_3$-acetone (4:1, v/v). Selected fractions containing the product ($R_f$ 0.29) were combined and concentrated to afford 1.23 g of a light-yellow oil. The 2.50 g lot was triturated with pentane (2×50 mL) in an ultrasonic bath and the pentane filtrate was concentrated. The resulting oil was purified by column chromatography on silica gel (50 g), eluting with $CHCl_3$-acetone (4:1, v/v). Selected fractions containing the product were combined and concentrated to give 0.58 g of a light-yellow oil. Impure fractions from the latter column were combined and concentrated, and the residue was chromatographed on silica gel (50 g) to give 0.28 g of a light-yellow oil. All purified materials were combined, concentrated and dried under high vacuum to yield 1.83 g (51.9%) of a light-yellow oil.

3-((3S)-3-Pyrrolidinyloxy)pyridine

Under a nitrogen atmosphere, a cold (0–5° C.), stirring solution of 3-((3S)-N-(tert-butoxycarbonyl)-3-pyrrolidinyloxy)pyridine (0.535 g, 2.024 mmol) in dry $CH_2Cl_2$ (5 mL, distilled from $LiAlH_4$) was treated drop-wise with trifluoroacetic acid (3 mL, 4.44 g, 38.94 mmol). After stirring 30 min at 0–5° C., the solution was concentrated by rotary evaporation. The residue was acidified with 1 M HCl solution (15 mL) and extracted with toluene (4×25 mL) to remove impurities (triphenylphosphine oxide). At 0–5° C., the aqueous layer was basified with 1 M NaOH solution to pH 12. The mixture was saturated with NaCl and extracted with $CHCl_3$ (8×20 mL). The combined $CHCl_3$ extracts were dried ($Na_2SO_4$), filtered, concentrated by rotary evaporation and briefly dried under high vacuum to give 240 mg (72.3%) of a light-yellow oil.

3-((3S)-3-Pyrrolidinyloxy)pyridine Dihydrochloride

Concentrated HCl (2 mL) was added drop-wise to 3-((3S)-3-pyrrolidinyloxy)pyridine (240 mg, 1.462 mmol), and the resulting solution was concentrated by rotary evaporation. Ethanol was added to the residue and removed by rotary evaporation to dry the product. The procedure was repeated several times until a solid was obtained. Ethanol (1 mL) was added, and the resulting solution was treated with hot 2-propanol producing a precipitate. The solution was allowed to cool to ambient temperature and was further cooled at 5° C. for 48 h. The solids were filtered and dried under vacuum at 40° C. for 16 h to afford 215 mg (62.0%) of a hygroscopic, light-brown, granular solid, mp 145–148° C., $[\alpha]^{20.5}_D$+26.67° (c1.0, MeOH). The compound exhibits a Ki of 230 nM.

Example 37

Synthesis of 3-(1-Methyl-4-piperidinyloxy)pyridine 3-(1-Methyl-4-piperidinyloxy)pyridine Under a nitrogen atmosphere, a solution of diethyl azodicarboxylate (6.80 g. 39.0 mmol) in tetrahydrofuran (THF) (25 mL) was added drop-wise at ambient temperature to a stirring solution of triphenylphosphine (10.23 g, 390 mmol) in THF (100 mL). The resulting solution was allowed to stir at ambient temperature for 30 min. 4-Hydroxy-1- methylpiperidine (3.05 g, 26.5 mmol) and 3-hydroxypyridine (3.71 g, 39.0 mmol) were added, and the reaction mixture was stirred at ambient temperature for 18 h. The solution was concentrated by rotary evaporation, and the resulting residue was dissolved in CHCl₃ (100 mL). The suspension was cooled in an ice-water bath, and a solution of 1 M HCl (75 mL) was added with stirring. The aqueous phase was separated. The organic phase was extracted with water (3×75 mL). The combined aqueous extracts were cooled in an ice-water bath, basified with 1 M NaOH solution (125 mL) to pH ~11 and extracted with CHCl₃ (6×50 mL). The combined organic extracts were dried (Na₂SO₄), filtered, and concentrated by rotary evaporation. The crude product was dissolved in CHCl₃ (75 mL), and the CHCl₃ solution was extracted with 1 M NaOH solution (4×25 mL) to remove residual 3-hydroxypyridine. The CHCl₃ phase was separated, and the combined NaOH layers were back extracted with CHCl₃ (3×50 mL). All CHCl₃ extracts were combined, dried (Na₂SO₄), filtered, and concentrated by rotary evaporation. The resulting oil was purified by vacuum distillation using a test-tube distillation apparatus, collecting the fraction with bp 83–93° C. at 0.10–0.075 mm Hg. Further purification by a second vacuum distillation yielded 120 mg (2.4%) of a colorless oil, bp 72–75° C. at 0.75 mm Hg. The compound exhibits a Ki of 4897 nM.

Example 38
Synthesis of (2-(5-Bromo(3-pyridylthio))ethyl)methylamine
2-(5-Bromo-3-pyridylthio)ethan-1-ol Under a nitrogen atmosphere, a mixture of 2-mercaptoethanol (3.30 g, 42.21 mmol), sodium hydroxide (1.69 g, 42.21 mmol) and N,N-dimethylformamide (50 mL) was stirred at ambient temperature for 4 h. The resulting solution was cooled to 0–5° C. and 3,5-dibromopyridine (8.00 g, 33.77 mmol) was added in one portion. The mixture was stirred at 0–5° C. for 20 min, warmed to ambient temperature and further stirred for 1 h. TLC analysis on silica gel eluting with EtOAc-hexane (3:1) indicated an incomplete reaction. Therefore, the mixture was heated at 75° C. (oil bath temperature) for 1 7 h. After cooling to ambient temperature, the mixture was poured into water (250 mL) and extracted with ether (3×75 mL). The combined ether extracts were dried (Na₂SO₄), filtered and concentrated (rotary evaporator) to a light-yellow oil. The oil was vacuum distilled using a short-path distillation apparatus to afford 4.55 g (57.5%) of a light-yellow oil, bp 138–140° C. at 0.35 mm Hg.

(2-(5-Bromo(3-pyridylthio))ethyl)methylamine

Under a nitrogen atmosphere, a cold (0–5° C.), stirring solution of 2-(5-bromo-3-pyridylthio)ethan-1-ol (1.00 g, 4.27 mmol) in dichloromethane (4 mL) containing pyridine (3 drops) was treated in one portion with p-toluenesulfonyl chloride (0.855 g, 4.49 mmol). The resulting solution was allowed to warm to ambient temperature over 16 h. The solution was concentrated on a rotary evaporator, and the oily residue was dried under high vacuum to give a light-beige solid. The solid was partitioned between saturated K₂CO₃ solution (12 mL) and CHCl₃ (10 mL). The CHCl₃ phase was separated and the aqueous phase was extracted with CHCl₃ (3×10 mL). All CHCl₃ extracts were combined and washed with saturated NaCl solution (10 mL). The CHCl₃ extracts were concentrated (rotary evaporator) to an oil that was dried under high vacuum to yield a light beige solid (1.83 g). The solid was transferred to a heavy-walled glass pressure-tube apparatus with methanol (10 mL), and a 40 wt % aqueous solution of methylamine (26 mL) was added. The tube was sealed and the mixture was stirred and heated at 115° C. (oil bath temperature) for 45 min. The resulting solution was allowed to cool to ambient temperature and was further stirred for 16 h. The solution was concentrated on a rotary evaporator. The resulting oil was basified with 1 M NaOH solution (10 mL) and extracted with CHCl₃ (4×10 mL). The combined CHCl₃ extracts were washed with saturated NaCl solution (10 mL), dried (Na₂SO₄), filtered and concentrated to a brown oil (1.22 g). The crude product was purified by column chromatography on silica gel (50 g), eluting with EtOAc-hexane (3:1, v/v) to collect 2-(5-bromo-3-pyridylthio)ethan-1-ol ($R_f$ 0.25) (0.47 g). Further elution with MeOH-Et₃N (97:3, v/v) afforded 0.38 g (35.6%) of (2-(5-bromo(3-pyridylthio))ethyl) methylamine ($R_f$ 0.49) as a light-yellow oil.

(2-(5-Bromo(3-pyridylthio))ethyl)methylamine Hemigalactarate

To a solution of (2-(5-bromo(3-pyridylthio))ethyl) methylamine (352.3 mg, 1.43 mmol) in ethanol (5 mL) was added galactaric acid (150.0 mg, 0.71 mmol). Water (2 mL) was added drop-wise, while gently warming the solution. To remove some white, insoluble crystals, the warm solution was filtered through a glass wool plug, washing the filter plug with a warm solution of ethanol-water (4:1, v/v) (2 mL). The filtrate was diluted with ethanol (9.5 mL), producing a white precipitate. The mixture was allowed to cool to ambient temperature and was further cooled at 5° C. for 48 h. The precipitate was filtered, washed with ethanol (4 mL) and vacuum dried at 45° C. for 18 h to give 437.5 mg (87.2%) of a white, crystalline powder, mp 161.5–166° C. (d). The compound exhibits a Ki of 3400 nM.

The foregoing is illustrative of the present invention and is not to be construed as limiting thereof. The invention is defined by the following claims, with equivalents of the claims to be included therein.

That which is claimed is:

1. A compound of the formula:

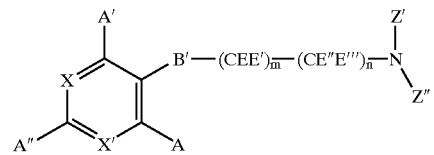

where
X' is N and X is selected from the group consisting of C—H, C—F, C—Cl, C—Br, C—I, C—R', C—NR'R", C—CF₃, C—OH, C—CN, C—NO₂, C—C₂R', C—SH, C—SCH₃, C—N₃, C—SO₂CH₃, C—OR', C—SR', C—C(=O)NR'R", C—NR'C(=O)R', C—C(=O)R', C—C(=O)OR', C(CH₂)$_q$OR', C—OC(=O)R', COC(=O)NR'R" and C—NR'C(=O)OR' where R' and R" are individually hydrogen, lower alkyl, an aromatic group-containing species, or a substituted aromatic group-containing species, and q is an integer from 1 to 6; m is an integer and n is an integer such that the sum of m plus n is 1, 2, 3, 4, 5, 6, 7, or 8; Z' and Z" individually represent hydrogen or lower alkyl; E, E', E" and E'" individually represent hydrogen or a non-hydrogen substituent selected from the group consisting of alkyl, substituted alkyl, halo substituted alkyl, cycloalkyl, substituted cycloalkyl, heterocycl, substituted heterocycl, aryl, substituted aryl, alkylaryl, substituted alkylaryl, arylalkyl and substituted arylakyl;
when n is 1, Z' and E'" and the associated carbon and nitrogen atoms can combine to form a monocyclic ring structure;

A, A' or A" are individually hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl and substituted arylalkyl functionalities;

when X is carbon bonded to a substituent component, A' or A" can combine with the substituent component to form a saturated or unsaturated, substituted or unsubstituted carbocyclic or heterocyclic ring;

when X' is carbon bonded to a substituent component, A or A" can combine with the substituent component to form a saturated or unsaturated, substituted or unsubstituted carbocyclic or heterocyclic ring; B' is sulfur or oxygen, and wherein the term substituted as used in defining E, E', E" and E''' and A, A' and A" refers to one or more substituents identified above in connection with the definition of X.

2. The compound according to claim 1, wherein B' is oxygen.

3. The compound according to claim 2, wherein n is 1, and wherein Z' and E''' and the associated carbon and nitrogen atoms combine to form a monocyclic ring structure.

4. The compound according to claim 3, wherein m is 0.

5. The compound according to claim 3, wherein Z" and E''' are each selected from the group consisting of methylene and ethylene.

6. The compound according to claim 2, selected from the group consisting of 3-(4-piperidinyloxy)pyridine, 3-(1-methyl-4-piperidinyloxy)pyridine, and 3-(3-pyrrolidinyloxy)pyridine.

7. The method according to claim 1, wherein B' is sulfur.

8. The compound according to claim 7, wherein the sum of m plus n is 2.

9. The compound according to claim 7, wherein one of Z' and Z" is hydrogen and the other is lower alkyl.

10. The compound according to claim 7, wherein X is C—Br.

11. The compound according to claim 7, (2-(5-bromo-(3-pyridylthio)ethyl)methylamine.

12. A method of treating a central nervous system disorder which is characterized by an alteration in normal neurotransmitter release, said method comprising administering to a subject in need thereof, an effective amount of a compound of the formula:

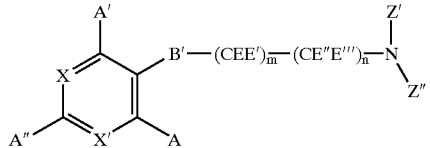

where

X' is N and X is selected from the group consisting of C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen, lower alkyl, an aromatic group-containing species, or a substituted aromatic group-containing species, and q is an integer from 1 to 6; m is an integer and n is an integer such that the sum of m plus n is 1, 2, 3, 4, 5, 6, 7, or 8; Z' and Z" individually represent hydrogen or lower alkyl; E, E', E" and E''' individually represent hydrogen or a non-hydrogen substituent selected from the group consisting of alkyl, substituted alkyl, halo substituted alkyl, cycloalkyl, substituted cycloalkyl, heterocycl, substituted heterocycl, aryl, substituted aryl, alkylaryl, substituted alkylaryl, arylalkyl and substituted arylakyl;

when n is 1, Z' and E''' and the associated carbon and nitrogen atoms can combine to form a monocyclic ring structure;

A, A' or A" are individually hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl and substituted arylalkyl functionalities;

when X is carbon bonded to a substituent component, A' or A" can combine with the substituent component to form a saturated or unsaturated, substituted or unsubstituted carbocyclic or heterocyclic ring;

when X' is carbon bonded to a substituent component, A or A" can combine with the substituent component to form a saturated or unsaturated, substituted or unsubstituted carbocyclic or heterocyclic ring; B' is sulfur or oxygen, and wherein the term substituted as used in defining E, E', E" and E''' and A, A' and A" refers to one or more substituents identified above in connection with the definition of X.

13. The method according to claim 12, wherein B' is oxygen.

14. The method according to claim 13, wherein n is 1, and wherein Z' and E''' and the associated carbon and nitrogen atoms combine to form a monocyclic ring structure.

15. The method according to claim 14, wherein m is 0.

16. The method according to claim 14, wherein Z" and E''' are each selected from the group consisting of methylene and ethylene.

17. The method according to claim 13, selected from the group consisting of 3-(4-piperidinyloxy)pyridine, 3-(1-methyl-4-piperidinyloxy)pyridine, and 3-(3-pyrrolidinyloxy)pyridine.

18. The method according to claim 12, wherein B' is sulfur.

19. The method according to claim 18, wherein the sum of m plus n is 2.

20. The method according to claim 18, wherein one of Z' and Z" is hydrogen and the other is lower alkyl.

21. The method according to claim 18, wherein X is C—Br.

22. The method according to claim 18, (2-(5-bromo-(3-pyridylthio)ethyl)methylamine.

23. A pharmaceutical composition incorporating a compound of the formula:

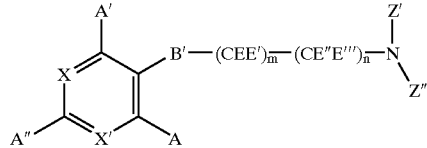

where

X' is N and X is selected from the group consisting of C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen, lower alkyl, an aromatic group-containing species, or a substituted aromatic group-containing species, and q is an integer from 1 to 6; m is an integer and n is an integer such that the sum of m plus n is 1, 2, 3, 4, 5, 6, 7, or 8; Z' and Z" individually represent hydrogen or lower alkyl; E, E', E" and E''' individually represent hydrogen or a non-hydrogen substituent selected from the group consisting of alkyl, substitute, halo substituted alkyl, cycloalkyl, substituted cycloalkyl, heterocycl, substituted heterocycl, aryl, substituted aryl, alkylaryl, substituted alkylaryl, arylalkyl and substituted arylakyl;

when n is 1, Z' and E''' and the associated carbon and nitrogen atoms can combine to form a monocyclic ring structure;

A, A' or A" are individually hydrogen, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl and substituted arylalkyl functionalities;

when X is carbon bonded to a substituent component, A' or A" can combine with the substituent component to form a saturated or unsaturated, substituted or unsubstituted carbocyclic or heterocyclic ring;

when X' is carbon bonded to a substituent component, A or A" can combine with the substituent component to form a saturated or unsaturated, substituted or unsubstituted carbocyclic or heterocyclic ring; B' is sulfur or oxygen, and wherein the term substituted as used in defining E, E', E" and E''' and A, A' and A" refers to one or more substituents identified above in connection with the definition of X.

24. The pharmaceutical composition according to claim 23, wherein in the compound B' is oxygen.

25. The pharmaceutical composition according to claim 24, wherein in the compound n is 1, and wherein Z' and E''' and the associated carbon and nitrogen atoms combine to form a monocyclic ring structure.

26. The pharmaceutical composition according to claim 25, wherein in the compound m is 0.

27. The pharmaceutical composition according to claim 25, wherein in the compound Z" and E''' are each selected from the group consisting of methylene and ethylene.

28. The pharmaceutical composition according to claim 24, selected from the group consisting of 3-(4-piperidinyloxy)pyridine, 3-(1-methyl-4-piperidinyloxy)pyridine, and 3-(3-pyrrolidinyloxy)pyridine.

29. The pharmaceutical composition according to claim 23, wherein in the compound B' is sulfur.

30. The pharmaceutical composition according to claim 29, wherein in the compound the sum of m plus n is 2.

31. The pharmaceutical composition according to claim 29, wherein in the compound one of Z' and Z" is hydrogen and the other is lower alkyl.

32. The pharmaceutical composition according to claim 29, wherein in the compound X is C—Br.

33. The pharmaceutical composition according to claim 29, (2-(5-bromo-(3-pyridylthio)ethyl)methylamine.

* * * * *